(12) United States Patent
Kaspar et al.

(10) Patent No.: US 12,357,663 B2
(45) Date of Patent: *Jul. 15, 2025

(54) INTRATHECAL DELIVERY OF RECOMBINANT ADENO-ASSOCIATED VIRUS ENCODING METHYL-CpG BINDING PROTEIN 2

(71) Applicants: NATIONWIDE CHILDREN'S HOSPITAL, INC., Columbus, OH (US); OHIO STATE INNOVATION FOUNDATION, Columbus, OH (US)

(72) Inventors: Brian K. Kaspar, Westerville, OH (US); Kevin Foust, Columbus, OH (US)

(73) Assignees: NATIONWIDE CHILDREN'S HOSPITAL, INC., Columbus, OH (US); OHIO STATE INNOVATION FOUNDATION, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/149,151

(22) Filed: Jan. 2, 2023

(65) Prior Publication Data

US 2023/0321164 A1 Oct. 12, 2023

Related U.S. Application Data

(63) Continuation of application No. 16/461,837, filed as application No. PCT/US2017/062371 on Nov. 17, 2017, now Pat. No. 11,583,564.

(60) Provisional application No. 62/423,618, filed on Nov. 17, 2016.

(51) Int. Cl.

| C12N 15/86 | (2006.01) |
| A61K 9/00 | (2006.01) |
| A61K 35/76 | (2015.01) |
| A61K 48/00 | (2006.01) |
| A61P 25/00 | (2006.01) |
| C07K 14/47 | (2006.01) |
| C12N 7/00 | (2006.01) |

(52) U.S. Cl.
CPC ............ *A61K 35/76* (2013.01); *A61K 9/0019* (2013.01); *A61K 9/0085* (2013.01); *A61P 25/00* (2018.01); *C07K 14/4702* (2013.01); *C12N 7/00* (2013.01); *C12N 2750/14132* (2013.01); *C12N 2750/14143* (2013.01)

(58) Field of Classification Search
CPC .............................. C12N 15/86; A61K 48/00
See application file for complete search history.

(56) References Cited

U.S. PATENT DOCUMENTS

| 5,173,414 A | 12/1992 | Lebkowski et al. |
| 5,658,776 A | 8/1997 | Flotte et al. |
| 5,786,211 A | 7/1998 | Johnson |
| 5,871,982 A | 2/1999 | Wilson et al. |
| 6,258,595 B1 | 7/2001 | Gao et al. |
| 6,566,118 B1 | 5/2003 | Atkinson et al. |
| 7,198,951 B2 | 4/2007 | Gao et al. |
| 9,415,121 B2 | 8/2016 | Kaspar et al. |
| 11,583,564 B2* | 2/2023 | Kaspar et al. ......... A61K 35/76 |
| 2005/0053922 A1 | 3/2005 | Schaffer et al. |
| 2009/0202490 A1 | 8/2009 | Schaffer et al. |
| 2009/0246768 A1 | 10/2009 | Sawalha et al. |
| 2013/0225666 A1* | 8/2013 | Kaspar et al. ..... A61K 48/0075 514/44 R |
| 2016/0038613 A1 | 2/2016 | Kaspar et al. |
| 2020/0181646 A1 | 6/2020 | Esteves et al. |

FOREIGN PATENT DOCUMENTS

| JP | 2012-010703 A | 1/2012 | |
| RU | 2273645 C2 | 4/2006 | |
| RU | 2502800 C2 | 12/2013 | |
| WO | 95/13365 A1 | 5/1995 | |
| WO | 95/13392 A1 | 5/1995 | |
| WO | 96/17947 A1 | 6/1996 | |
| WO | 97/06243 A1 | 2/1997 | |
| WO | 97/08298 A1 | 3/1997 | |
| WO | 97/09441 A2 | 3/1997 | |
| WO | 97/21825 A1 | 6/1997 | |
| WO | 98/09657 A2 | 3/1998 | |
| WO | 99/11764 A2 | 3/1999 | |
| WO | 01/05992 A1 | 1/2001 | |
| WO | WO2016100575 A1 * | 6/2016 | ............. A61K 48/00 |

OTHER PUBLICATIONS

Gray et al. (2012) "Design and Construction of Functional AAV Vectors" In: Snyder, R., Moullier, P. (eds) Adeno-Associated Virus, Methods in Molecular Biology, vol. 807. Humana Press. https://doi.org/10.1007/978-1-61779-370-7_2. (Year: 2012).*

Adachi et al., A segment of the Mecp2 promoter is sufficient to drive expression in neurons, Human Molecular Genetics, 14:3709-3722 (2005).

Armstrong et al., Selective dendritic alterations in the cortex of Rett syndrome, Journal of Neuropathology and Experimental Neurology, 54:195-201 (1995).

Bogoslovskaya, Bezopasnost' ispol'zovaniya retrovirusnyh vektorov v gennoj terapii, Vestnik RAMN., 10:55-61 (2012).

CCDS Database Entry #41016.1, Mus Musculus, dated Nov. 28, 2007.

Chahrour et al., MeCP2, a key contributor to neurological disease, activates and represses transcription, Science, 320:1224-1229 (2008).

Chen et al., Deficiency of methyl-CpG binding protein-2 in CNS neurons results in a Rett-like phenotype in mice, Nature Genetics, 27:327-331 (2001).

Ebert et al., Activity-dependent phosphorylation of MeCP2 threonine 308 regulates interaction with NCoR, Nature, 499:341-345 (2013).

(Continued)

*Primary Examiner* — James Joseph Graber
(74) *Attorney, Agent, or Firm* — MARSHALL, GERSTEIN & BORUN LLP

(57) ABSTRACT

Methods and materials for intrathecal delivery of recombinant Adeno-associated virus 9 (rAAV9) encoding Methyl-CpG binding protein 2 (MECP2) are provided. Use of the methods and materials is contemplated, for example, for the treatment of Rett syndrome.

24 Claims, 25 Drawing Sheets

Specification includes a Sequence Listing.

(56) References Cited

OTHER PUBLICATIONS

European Application No. 17872045.4, European Search Report and Opinion, mailed Jul. 9, 2020.
Gadalla et al., Improved Survival and Reduced Phenotypic Severity Following AAV9/MECP2 Gene Transfer to Neonatal and Juvenile Male Mecp2 Knockout Mice, Mol. Ther., 21(1):18-30 (2012).
Gao et al., Clades of Adeno-associated viruses are widely disseminated in human tissues, J. Virol., 78:6381-6388 (2004).
Garg et al., Systemic delivery of MeCP2 rescues behavioral and cellular deficits in female mouse models of Rett syndrome, J. Neurosci. 33:13612-13620 (2013).
GenBank Accession No. NC_000086.7, Mus musculus strain C57BL/6J chromosome X, GRCm38.p6 C57BL/6J, Aug. 8, 2019.
Guy et al., A mouse Mecp2-null mutation causes neurological symptoms that mimic Rett syndrome, Nature Genetics, 27:322-326 (2001).
Guy et al., Reversal of neurological defects in a mouse model of Rett syndrome, Science, 315:1143-1147 (2007).
Guy et al., The role of MeCP2 in the brain, Annual Review of Cell and Developmental Biology, 27:631-652 (2011).
Hardwick et al., Delineation of large deletions of the MECP2 gene in Rett syndrome patients, including a familial case with a male proband, European Journal of Human Genetics, 15:1218-1229 (2007).
International Preliminary Report on Patentability received for PCT Patent Application No. PCT/US2017/062371, mailed on May 31, 2019, 6 pages.
International Search Report and Written Opinion received for PCT Patent Application No. PCT/US2017/062371, mailed on Feb. 22, 2018, 8 pages.
Katz et al., Preclinical research in Rett syndrome: setting the foundation for translational success, Dis. Model Mech., 5:733-745 (2012).
Katz et al., Rett Syndrome: Crossing the Threshold to Clinical Translation, Trends in Neurosciences, 39:100-113 (2016).
Leonard et al., Clinical and biological progress over 50 years in Rett syndrome, Nature Reviews Neurology, 13:37-51 (2017).
Li et al., MECP2 and CDKL5 gene mutation analysis in Chinese patients with Rett syndrome, Journal of Human Genetics, 52:38-47 (2007).
Lioy et al., A role for glia in the progression of Rett's syndrome, Nature, 475:497-500 (2011).
Lombardi et al., MECP2 disorders: from the clinic to mice and back, The Journal of Clinical Investigation, 125:2914-2923 (2015).
Lyst et al., Rett syndrome mutations abolish the interaction of MeCP2 with the NCoR/SMRT co-repressor, Nature Neuroscience, 16:898-902 (2013).
Meyer et al., Improving single injection CSF delivery of AAV9-mediated gene therapy for SMA: a dose-response study in mice and nonhuman primates, Molecular Therapy: The Journal of the American Society of Gene Therapy, 23:477-487 (2015).
Muzyczka, Use of adeno-associated virus as a general transduction vector for mammalian cells, Current Topics in Microbiology and Immunology, 158:97-129 (1992).
Nan et al., The biological functions of the methyl-CpG-binding protein MeCP2 and its implication in Rett syndrome, Brain Development, 23, Suppl 1:S32-37 (2001).
Neul et al., Rett syndrome: revised diagnostic criteria and nomenclature, Ann. Neurol., 68:944-950 (2010).
Ross et al., Exclusive expression of MeCP2 in the nervous system distinguishes between brain and peripheral Rett syndrome-like phenotypes, Human Molecular Genetics, 25:4389-4404 (2016).
Ruffing et al., Mutations in the carboxy terminus of adeno-associated virus 2 capsid proteins affect viral infectivity: lack of an RGD integrin-binding motif, J. Gen. Virol., 75:3385-3392 (1994).
Srivastava et al., Nucleotide sequence and organization of the adeno-associated virus 2 genome, J. Virol., 45:555-564 (1983).
Weaving et al., Rett syndrome: clinical review and genetic update, Journal of Medical Genetics, 42:1-7 (2005).

\* cited by examiner

INTRATHECAL DELIVERY OF RECOMBINANT ADENO-ASSOCIATED VIRUS ENCODING METHYL-CpG BINDING PROTEIN 2

The present application is a divisional of U.S. application Ser. No. 16/461,837, filed May 17, 2019 which claims the benefit of priority of U.S. Provisional Patent Application No. 62/423,618 filed Nov. 17, 2016, both of which are incorporated herein by reference in their entirety.

INCORPORATION BY REFERENCE OF MATERIAL SUBMITTED ELECTRONICALLY

Incorporated by reference in its entirety is a sequence listing in computer-readable form submitted concurrently herewith and identified as follows: ASCII text file named "50215B_SeqListing.XML", 33,350 bytes, created Dec. 12, 2022.

FIELD OF THE INVENTION

The present invention relates to methods and materials for the intrathecal delivery of recombinant Adeno-associated virus 9 (rAAV9) encoding Methyl-CpG binding protein 2 (MECP2). Use of the methods and materials is contemplated, for example, for the treatment of Rett syndrome.

BACKGROUND

Rett syndrome is a neurodevelopmental X linked dominant disorder affecting ~1 in 10,000 girls. Hemizygous males usually die of neonatal encephalopathy. Heterozygous females survive into adulthood but exhibit severe symptoms including microcephaly, loss of purposeful hand motions and speech, and motor abnormalities which appear following a period of apparently normal development. Age of onset is around 6-18 months.

Rett syndrome is classified as Typical (or Classic) Rett or Atypical Rett. Spontaneous mutations gene encoding the transcription factor Methyl-CpG binding protein 2 (MECP2) cause the majority (~90%) of cases in both classifications although Atypical Rett can be caused by mutations in genes other than MECP2. The nature of the MECP2 mutation (e.g. deletion vs. point mutation) and skewed X chromosome inactivation impact disease severity. The MECP2 transcription factor modulates transcription of thousands of genes. Therapeutic efforts have focused on targets downstream of MECP2 including neurotransmitters, growth factors and metabolic pathways. At least nine clinical trials directed toward Rett syndrome have reported positive outcomes across different measures, but the findings have not been independently validated or resulted in new treatments [Katz et al, *Trends in Neurosciences*, 39:100-113 (2016)]. There are currently no approved therapies for Rett Syndrome.

There are male and female mouse models in which the mice exhibit RTT-like behaviors [Guy et al., *Nature Genetics*, 27: 322-326 (2001); Chen et al., *Nature Genetics* 27: 327-331 (2001); and Katz et al., 5: 733-745 (2012)].

MECP2 is a 52 kD nuclear protein that is expressed in a variety of tissues but is enriched in neurons and has been studied most in the nervous system. There are two isoforms of MECP2 in humans known as MECP2A and B (FIG. 1) [Weaving et al., *Journal of Medical Genetics*, 42: 1-7 (2005)]. The two isoforms derive from alternatively spliced mRNA transcripts and have different translation start sites. MECP2B includes exons 1, 3 and 4 and is the predominant isoform in the brain. MECP2 reversibly binds to methylated DNA and modulates gene expression [Guy et al., *Annual Review of Cell and Developmental Biology*, 27: 631-652 (2011)] These functions map to the methyl binding domain (MBD) and transcriptional repressor domain (TRD), respectively [Nan & Bird, Brain & Development, 23, Suppl 1: S32-37 (2001)]. Originally thought of as a transcriptional repressor, MECP2 can both induce and suppress target gene expression [Chahrour et al., *Science*, 320: 1224-1229 (2008)]. MECP2 is hypothesized to support proper neuronal development and maintenance. In neurons, MECP2 facilitates translation of synaptic activity into gene expression through DNA binding and interaction with different binding partners [Ebert et al., *Nature*, 499: 341-345 (2013) and Lyst et al., *Nature Neuroscience*, 16: 898-902 (2013)]. In astrocytes, MECP2 deficiency is linked to apneic events in mice [Lioy et al., *Nature*, 475: 497-500 (2011)]. MECP2 deficiency can cause reduced brain size, increased neuronal packing density and reduced dendritic complexity [Armstrong et al., *Journal of Neuropathology and Experimental Neurology*, 54: 195-201 (1995)]. Importantly, neuron death is not associated with MECP2 deficiency [Leonard et al., *Nature Reviews, Neurology*, 13: 37-51 (2017)]. MECP2 is also found outside the nervous system though levels vary across tissues (FIG. 2). A recent study examined the dependence of Rett symptoms in mice on peripheral Mecp2 expression [Ross et al., *Human Molecular Genetics*, 25: 4389-4404 (2016)]. Peripheral deficiency was associated with hypo-activity, exercise fatigue and bone abnormalities. The majority of RTT-associated behavioral, sensorimotor, gait and autonomic (respiratory and cardiac) phenotypes were absent in mice with peripheral MECP2 knock out.

Because MECP2 is an X-linked gene, one copy of MECP2 is silenced due to X chromosome inactivation (Xci) in females. On a per cell basis, Xci is believed to be random which leads to MECP2 chimerism in Rett females. Disease severity is impacted by whether the majority of active X chromosomes contain the intact or mutated MECP2 gene. This is called skewed Xci. Males do not undergo Xci, therefore MECP2 deficiency is more severe as no cells will have a functional copy of MECP2. The nature of the MECP2 mutation also impacts disease severity. Over 600 different mutations of the MECP2 gene are described in the RettBASE database including deletions, non-sense and point mutations. The most common mutation (~9% of patients) is the Ti 85M allele which affects the methyl binding domain. Other common mutations are shown in FIG. 3 [Leonard, supra]. Together these account for over 40% of cases listed in RettBASE. Large scale deletions involving MECP2 were found in 8-10% of cases [Li et al., *Journal of Human Genetics*, 52: 38-47 (2007) and Hardwick et al., *European Journal of Human Genetics*, 15:1218-1229 (2007)]. There is genotype-phenotype correlation with R133C, R294X and C-terminal mutations and deletions (downstream of the TRD) causing milder disease. Large deletions and early truncating mutations (R270X, R255X and R168X) are associated with severe Rett syndrome. Table 1 describes consensus Rett diagnostic criteria recently compiled by a group of international Rett clinicians [Neul et al., *Annals of Neurology*, 68: 944-950 (2010)].

TABLE 1

RTT Diagnostic Criteria 2010-Consider diagnosis when postnatal deceleration of head growth observed.

Required for typical or classic RTT
1. A period of regression followed by recovery or stabilization.*
2. All main criteria and all exclusion criteria
3. Supportive criteria are not required, although often present in typical RTT Required for atypical or variant RTT
1. A period of regression followed by recovery or stabilization
2. At least 2 out of the 4 main criteria
3. 5 out of 11 supportive criteria Main Criteria
1. Partial or complete loss of acquired purposeful hand skills.
2. Partial or complete loss of acquired spoken language**
3. Gait abnormalities: Impaired (dyspraxic) or absence of ability.
4. Stereotypic hand movements such as hand wringing/squeezing, clapping/tapping, mouthing and washing/rubbing automatisms.

Exclusion Criteria for RTT
1. Brain injury secondary to trauma (peri- or postnatally), neurometabolic disease, or severe infection that causes neurological problems***
2. Grossly abnormal psychomotor development in first 6 months of life#

Supportive Criteria for atypical RTT##
  Breathing disturbances when awake
  Bruxism when awake
  Impaired sleep pattern
  Abnormal muscle tone
  Peripheral vasomotor disturbances
  Scoliosis/kyphosis
  Growth retardation
  Small cold hands and feet
  Inappropriate laughing/screaming spells
  Diminished response to pain
  Intense eye communication- "eye pointing"

*= Because MECP2 mutations are now identified in some individuals prior to any clear evidence of regression, the diagnosis of "possible" RTT should be given to those individuals under 3 years old who have not lost any skills but otherwise have clinical features suggestive of RTT. These individuals should be reassessed every 6-12 months for evidence of regression. If regression manifests, the diagnosis should then be changed to definite RTT. However, if the child does not show any evidence of regression by 5 years, the diagnosis of RTT should be questioned.
**= Loss of acquired language is based on best acquired spoken language skill, not strictly on the acquisition of distinct words or higher language skills. Thus, an individual who had learned to babble butthen loses this ability is considered to have loss of acquired language.
***= There should be clear evidence (neurological or ophthalmological examination and MRI/CT) that the presumed insult directly resulted in neurological dysfunction.
= Grossly abnormal to the point that normal milestones (acquiring head control, swallowing, developing social smile) are not met. Mild generalized hypotonia or other previously reported subtle developmental alterations during the first six months of life is common in RTT and do not constitute an exclusionary criterion.
= If an individual has or ever had a clinical feature listed it is counted as a supportive criterion. Many of these features have an age dependency, manifesting and becoming more predominant at certain ages. Therefore, the diagnosis of atypical RTT may be easier for older individuals than for younger. In the case of a younger individual (under 5 years old) who has a period of regression and ≥2 main criteria but does not fulfill the requirements of 5/11 supportive criteria, the diagnosis of "probably atypical RTT" may be given. Individuals who fall into this category should be reassessed as they age and the diagnosis revised accordingly.

Adeno-associated virus (AAV) is a replication-deficient parvovirus, the single-stranded DNA genome of which is about 4.7 kb in length including 145 nucleotide inverted terminal repeat (ITRs). The nucleotide sequence of the AAV serotype 2 (AAV2) genome is presented in Srivastava et al., *J Virol*, 45: 555-564 (1983) as corrected by Ruffing et al., *J Gen Virol*, 75: 3385-3392 (1994). Cis-acting sequences directing viral DNA replication (rep), encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection. Multiple serotypes of AAV exist and offer varied tissue tropism. Known serotypes include, for example, AAV1, AAV2, AAV3, AAV4, AAV5, AAV6, AAV7, AAV8, AAV9, AAV10, AAV11, AAV12, AAV13 and AAVrh74. AAV9 is described in U.S. Pat. No. 7,198,951 and in Gao et al., *J. Virol.*, 78: 6381-6388 (2004).

There remains a need in the art for methods and products for delivering MECP2 polynucleotides to, and expressing the polynucleotides in, the central nervous system.

SUMMARY

The present disclosure provides methods and materials useful for treating Rett syndrome in a patient in need thereof.

Methods are provided of treating Rett syndrome in a patient comprising the step of intrathecal administration of a recombinant adeno-associated virus 9 (rAAV9) encoding Methyl-CpG binding protein 2 (MECP2) to a patient in need thereof, wherein the rAAV9 comprises a self-complementary genome encoding MECP2B and wherein the sequence of the self-complementary genome is set out in SEQ ID NO: 1. An exemplary rAAV9 provided is the scAAV named AVXS-201.

Methods are provided which further comprise the step of intrathecal administration of iohexol, iobitridol, iomeprol, iopamidol, iopentol, iopromide, ioversol or ioxilan, or mixtures of two or more thereof, to the patient, and/or which further comprise putting the patient in the Trendelenberg position.

DETAILED DESCRIPTION

Figure 1:
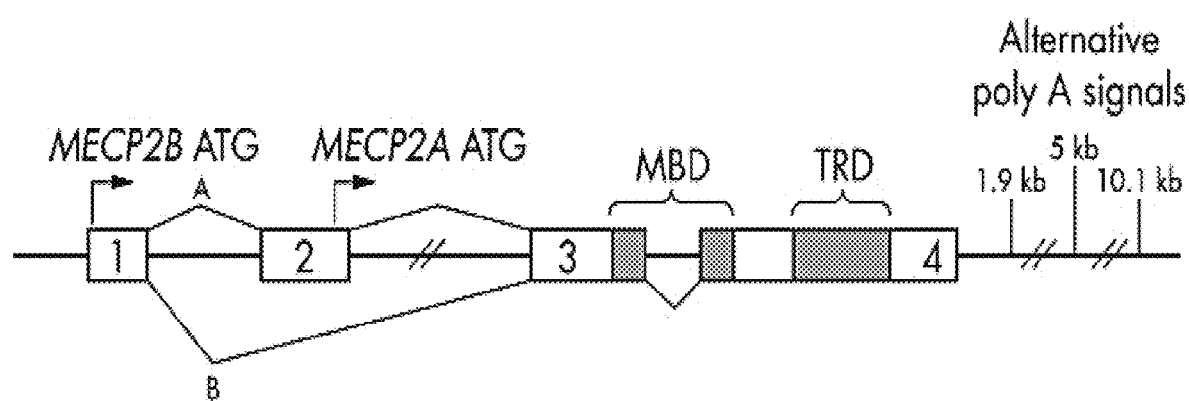
FIG. 1: Diagram of the human MECP2 locus. The picture shows the alternative transcription start sites (arrows), exons (boxes) and splicing pattern of the mature mRNAs. MECP2B is the isoform most abundant in the brain and is encoded by AVXS-201.
Figure 2:
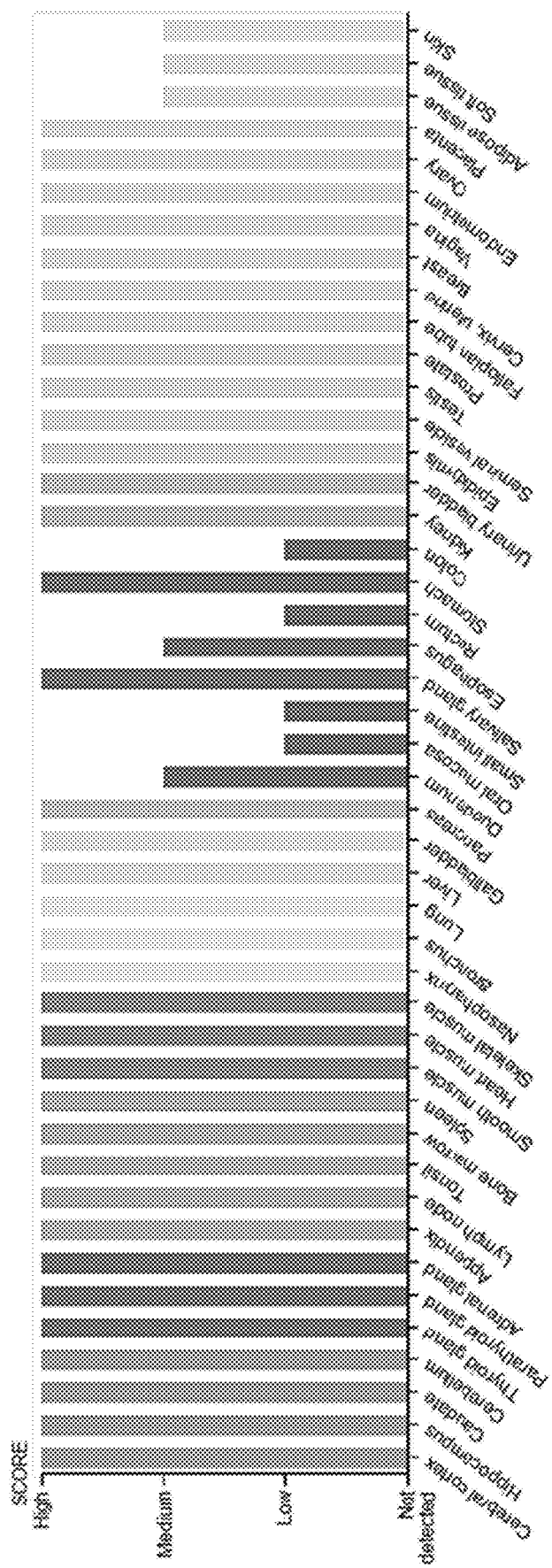
FIG. 2: Chart depicts relative MECP2 protein expression levels in various human tissues as detected by immunohistochemistry. Modified from The Human Protein Atlas (www.proteinatlas.org).
Figure 3:
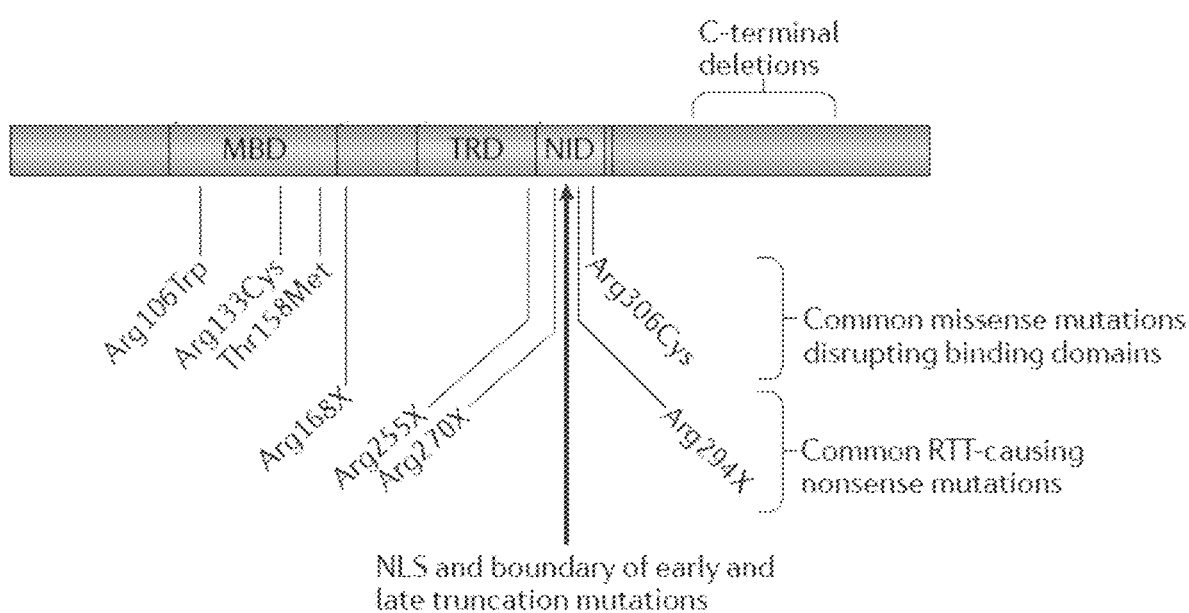
FIG. 3: Key functional domains of the MECP2 protein and common mutations found in Rett patients. MBD=methyl-CpG-binding, TRD=Transcriptional Repression Domain, NID=NCOR-SMRT interaction domain (NID), and the nuclear localization signal (NLS)

In one aspect, the invention provides methods for the intrathecal administration (i.e., administration into the space under the arachnoid membrane of the brain or spinal cord) of a polynucleotide encoding MECP2 to a patient comprising administering a rAAV9 with a genome including the polynucleotide. In some embodiments, the rAAV9 genome is a self-complementary genome. In other embodiments, the rAAV9 genome is a single-stranded genome.

The methods deliver the polynucleotide encoding MECP2 to the brain and spinal cord of the patient (i.e., the central nervous system of the patient). Some target areas of the brain contemplated for delivery include, but are not limited to, the motor cortex and the brain stem. Some target cells of the central nervous system contemplated for delivery include, but are not limited to, nerve cells and glial cells. Examples of glial cells are microglial cells, oligodendrocytes and astrocytes.

Delivery of polynucleotides encoding MECP2 is indicated, for example, for treatment of Rett Syndrome.

"Treatment" comprises the step of administering via the intrathecal route an effective dose, or effective multiple doses, of a composition comprising a rAAV of the invention to a subject animal (including a human patient) in need thereof. If the dose is administered prior to development of a disorder/disease, the administration is prophylactic. If the dose is administered after the development of a disorder/disease, the administration is therapeutic. In embodiments of the invention, an effective dose is a dose that alleviates (either eliminates or reduces) at least one symptom associated with the disorder/disease state being treated, improves at least one symptom associated with the disorder/disease state being treated, that slows or prevents progression to a disorder/disease state, that diminishes the extent of disease, that results in remission (partial or total) of disease, and/or that prolongs survival.

In treatment of Rett syndrome, the methods result in an effect in the subject including, but not limited to, regaining purposeful hand movements, improvement in speech, reduction in apneas, reduction in seizures, reduction in anxiety, increased socialization, increase in IQ, normalization of sleep patterns and/or increased mobility.

Combination treatments are also contemplated by the invention. Combination as used herein includes both simultaneous treatment or sequential treatment. Combinations of methods of the invention with standard medical treatments for Rett syndrome are specifically contemplated, as are combinations with novel therapies.

While delivery to an individual in need thereof after birth is contemplated, intrauterine delivery to a fetus is also contemplated.

In another aspect, the invention provides rAAV genomes. The rAAV genomes comprise one or more AAV ITRs flanking a polynucleotide encoding MECP2. The polynucleotide is operatively linked to transcriptional control DNAs, specifically promoter DNA and polyadenylation signal sequence DNA that are functional in target cells to form a "gene cassette." The gene cassette may include promoters that allow expression specifically within neurons or specifically within glial cells. Examples include neuron specific enolase and glial fibrillary acidic protein promoters. Inducible promoters under the control of an ingested drug may also be used. Examples include, but are not limited to, systems such as the tetracycline (TET on/off) system [Urlinger et al., *Proc. Natl. Acad. Sci. USA* 97(14):7963-7968 (2000)] and the Ecdysone receptor regulatable system [Palli et al., *Eur J. Biochem* 270: 1308-1315 (2003). The gene cassette may further include intron sequences to facilitate processing of an RNA transcript when the polynucleotide is expressed in mammalian cells.

The rAAV genomes of the invention lack AAV rep and cap DNA. AAV DNA in the rAAV genomes (e.g., ITRs) may be from any AAV serotype for which a recombinant virus can be derived including, but not limited to, AAV serotypes AAV1, AAV2, AAV3, AAV4, AAV5, AAV6, AAV7, AAV8, AAV9, AAV10, AAV11, AAV12, AAV13 and AAVrh74. The nucleotide sequences of the genomes of the AAV serotypes are known in the art. For example, the AAV9 genome is provided in Gao et al., *J. Virol.*, 78: 6381-6388 (2004).

In another aspect, the invention provides DNA plasmids comprising rAAV genomes of the invention. The DNA plasmids are transferred to cells permissible for infection with a helper virus of AAV (e.g., adenovirus, E1-deleted adenovirus or herpesvirus) for assembly of the rAAV genome into infectious viral particles with AAV9 capsid proteins. Techniques to produce rAAV particles, in which an AAV genome to be packaged, rep and cap genes, and helper virus functions are provided to a cell, are standard in the art. Production of rAAV requires that the following components are present within a single cell (denoted herein as a packaging cell): a rAAV genome, AAV rep and cap genes separate from (i.e., not in) the rAAV genome, and helper virus functions. Production of pseudotyped rAAV is disclosed in, for example, WO 01/83692 which is incorporated by reference herein in its entirety. In various embodiments, AAV capsid proteins may be modified to enhance delivery of the recombinant vector. Modifications to capsid proteins are generally known in the art. See, for example, US 2005/0053922 and US 2009/0202490, the disclosures of which are incorporated by reference herein in their entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595. The foregoing documents are hereby incorporated by reference in their entirety herein, with particular emphasis on those sections of the documents relating to rAAV production.

The invention thus provides packaging cells that produce replication-deficient, infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

Thus, in another aspect, the invention provides rAAV such as rAAV9 (i.e., replication-deficient, infectious encapsidated rAAV9 particles) comprising a rAAV genome of the invention. The genomes of the rAAV lack AAV rep and cap DNA, that is, there is no AAV rep or cap DNA between the ITRs of the genomes. In some embodiments, the rAAV genome is a self-complementary genome. In some embodiments, the rAAV genome is a single-stranded genome.

rAAV are provided such as a self-complementary AAV9 (scAAV9) named "AVXS-201." Its gene cassette (nucleotides 151-2558 of the AVXS-201 genome set out in SEQ ID NO: 1) has, in sequence, a 549 [546] bp promoter fragment (SEQ ID NO: 2) (nucleotides 74085586-74086323 of NO_000086.7 in the reverse orientation) from the mouse MECP2 gene, an SV40 intron, a human MECP2B cDNA (SEQ ID NO: 3) (CCDS Database #CCDS48193.1), and a synthetic polyadenylation signal sequence (SEQ ID NO: 4). The gene cassette is flanked by a mutant AAV2 inverted terminal repeat (ITR) and a wild type AAV2 inverted terminal repeat that together enable packaging of self-complementary AAV genomes. The genome lacks AAV rep and cap DNA, that is, there is no AAV rep or cap DNA between the ITRs of the genome.

rAAV are provided such as a scAAV9 named "scAAV9.738.Mecp2." Its gene cassette (nucleotides 198-2890 of the scAAV9.738.Mecp2 genome set out in SEQ ID NO: 5) has, in sequence, a 738 bp promoter fragment (SEQ ID NO: 6) (nucleotides 74085586-74086323 of NC_000086.7 in the reverse orientation) from the mouse MECP2 gene, an SV40 intron, a mouse MECP2a cDNA (SEQ ID NO: 7) (CCDS Database #CCDS41016.1), and a polyadenylation signal sequence from the bovine growth hormone gene. The gene cassette is flanked by a mutant AAV2 inverted terminal repeat (ITR) and a wild type AAV2 inverted terminal repeat that together enable packaging of self-complementary AAV genomes. The genome lacks AAV rep and cap DNA, that is, there is no AAV rep or cap DNA between the ITRs of the genome.

Conservative nucleotide substitutions in the rAAV9 genome including, but not limited to, in the gene cassette in the rAAV9 genome, are contemplated. For example, a MECP2 cDNA in a gene cassette may have 80%, 81%, 82%, 83%, 84%, 85%, 86%, 87%, 88%, 89%, 90%, 91%, 92%, 93%, 94%, 95%, 96%, 97%, 98% or 99% sequence identity to the MECP2a cDNA in scAAV9.738.Mecp2 or the MECP2B cDNA in AVXS-201.

In some embodiments, the MECP2 polypeptide encoded by a rAAV9 of the invention may be a variant MECP2 polypeptide. A variant polypeptide retains MECP2 activity and has an amino acid sequence at least about 60, 70, 80, 85, 90, 95, 97, 98, 99 or 99.5% identical to the amino acid sequence of the MECP2 polypeptide encoded by the MECP2a cDNA in scAAV9.738.Mecp2 or the MECP2B cDNA in AVXS-201.

The rAAV may be purified by methods standard in the art such as by column chromatography or cesium chloride gradients. Methods for purifying rAAV vectors from helper virus are known in the art and include methods disclosed in, for example, Clark et al., *Hum. Gene Ther.*, 10(6): 1031-1039 (1999); Schenpp and Clark, *Methods Mol. Med.*, 69: 427-443 (2002); U.S. Pat. No. 6,566,118 and WO 98/09657.

In another aspect, the invention contemplates compositions comprising a rAAV, such as a rAAV9, encoding a MECP2 polypeptide.

Compositions of the invention comprise rAAV in a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Titers and dosages of rAAV to be administered in methods of the invention will vary depending, for example, on the particular rAAV, the mode of administration, the treatment goal, the individual, the timing of administration, and the cell type(s) being targeted, and may be determined by methods standard in the art. Titers of rAAV may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg). These dosages of rAAV may range from about $1\times10^9$ vg or more, about $1\times10^{10}$ vg or more, about $1\times10^{11}$ vg or more, about $1\times10^{12}$ vg or more, about $6\times10^{12}$ or more, about $1\times10^{13}$ vg or more, about $1.3\times10^{13}$ vg or more, about $1.4\times10^{13}$ vg or more, about $2\times10^{13}$ vg or more, about $3\times10^{13}$ vg or more, about $6\times10^{13}$ vg or more, about $1\times10^{14}$ vg or more, about $3\times10^{14}$ or more, about $6\times10^{14}$ or more, about $1\times10^{15}$ vg or more, about $3\times10^{15}$ or more, about $6\times10^{15}$ or more, about $1\times10^{16}$ or more, about $3\times10^{16}$ or more, about $6\times10^{16}$ or more. For a neonate, the dosages of rAAV may range from about $1\times10^9$ vg or more, about $1\times10^{10}$ vg or more, about $1\times10^{11}$ vg or more, about $1\times10^{12}$ vg or more, about $6\times10^{12}$ or more, about $1\times10^{13}$ vg or more, about $1.3\times10^{13}$ vg or more, about $1.4\times10^{13}$ vg or more, about $2\times10^{13}$ vg or more, about $3\times10^{13}$ vg or more, about $6\times10^{13}$ vg or more, about $1\times10^{14}$ vg or more, about $3\times10^{14}$ or more, about $6\times10^{14}$ or more, about $1\times10^{15}$ vg or more, about $3\times10^{15}$ or more, about $6\times10^{15}$ or more, about $1\times10^{16}$ or more, about $3\times10^{16}$ or more, or about $6\times10^{16}$ or more.

The methods of the invention result in the transduction of target cells (including, but not limited to, nerve or glial cells). The term "transduction" is used to refer to the administration/delivery of a polynucleotide to a target cell either in vivo or in vitro, via a replication-deficient infectious rAAV of the invention resulting in expression of a functional MECP2 polypeptide by the recipient cell.

Transduction of cells using rAAV of the invention results in sustained expression of the MECP2 polypeptide encoded by the rAAV. In some embodiments, the target expression level is contemplated to be about 75% to about 125% of the normal (or wild type) physiological expression level in a subject who does not have Rett syndrome. The target expression level may be about 75%, about 80%, about 85%, about 90%, about 95%, about 100%, about 105%, about 110%, about 115%, about 120% or about 125% of the normal expression level.

In some embodiments of treatment methods of the invention, a non-ionic, low-osmolar contrast agent is also administered to the patient. Such contrast agents include, but are not limited to, iobitridol, iohexol, iomeprol, iopamidol, iopentol, iopromide, ioversol, ioxilan, and mixtures of two or more of the contrast agents. In some embodiments, the treatment methods thus further comprise administration of iohexol to the patient. The non-ionic, low-osmolar contrast agent is contemplated to increase transduction of target cells in the central nervous system of the patient. It is contemplated that the transduction of cells is increased when a rAAV of the disclosure is used in combination with a contrast agent as described herein relative to the transduction of cells when a rAAV of the disclosure is used alone. In various embodiments, the transduction of cells is increased by at least about 1%, or at least about 5%, at least about 10%, at least about 20%, at least about 30%, at least about 40%, at least about 50%, at least about 60%, at least about 70%, at least about 80%, at least about 90%, at least about 100%, at least about 120%, at least about 150%, at least about 180%, at least about 200%, at least about 250%, at least about 300%, at least about 350%, at least about 400%, at least about 450%, at least about 500% or more when a vector of the disclosure is used in combination with a contrast agent as described herein, relative to the transduction of a vector of the disclosure when not used in combination with a contrast agent. In further embodiments, the transduction of cells is increased by about 10% to about 50%, or by about 10% to about 100%, or by about 5% to about 10%, or by about 5% to about 50%, or by about 1% to about 500%, or by about 10% to about 200%, or by about 10% to about 300%, or by about 10% to about 400%, or by about 100% to about 500%, or by about 150% to about 300%, or by about 200% to about 500% when a vector of the disclosure is used in combination with a contrast agent as described herein, relative to the transduction of a vector of the disclosure when not used in combination with a contrast agent.

In some embodiments, it is contemplated that the transduction of cells is increased when the patient is put in the Trendelenberg position (head down position). In some embodiments, for example, the patients is tilted in the head down position at about 1 degree to about 30 degrees, about 15 to about 30 degrees, about 30 to about 60 degrees, about 60 to about 90 degrees, or about 90 up to about 180 degrees) during or after intrathecal vector infusion. In various embodiments, the transduction of cells is increased by at least about 1%, or at least about 5%, at least about 10%, at least about 20%, at least about 30%, at least about 40%, at least about 50%, at least about 60%, at least about 70%, at least about 80%, at least about 90%, at least about 100%, at least about 120%, at least about 150%, at least about 180%, at least about 200%, at least about 250%, at least about 300%, at least about 350%, at least about 400%, at least about 450%, at least about 500% or more when a the Trendelenberg position is used as described herein, relative to when the Trendelenberg position is not used.

In further embodiments, the transduction of cells is increased by about 10% to about 50%, or by about 10% to about 100%, or by about 5% to about 10%, or by about 5% to about 50%, or by about 1% to about 500%, or by about 10% to about 200%, or by about 10% to about 300%, or by about 10% to about 400%, or by about 100% to about 500%, or by about 150% to about 300%, or by about 200% to about 500% when a vector of the disclosure is used in combination with a contrast agent and the Trendelenberg position as described herein, relative to the transduction of a vector of the disclosure when not used in combination with a contrast agent and Trendelenberg position.

The disclosure also provides treatment method embodiments wherein the intrathecal administration of a vector of the disclosure and a contrast agent to the central nervous system of a patient in need thereof results in an increase in survival of the patient relative to survival of the patient when a vector of the disclosure is administered in the absence of the contrast agent. In various embodiments, administration of a vector of the disclosure and a contrast agent to the central nervous system of a patient in need thereof results in an increase of survival of the patient of at least about 1%, at least about 5%, at least about 10%, at least about 20%, at least about 30%, at least about 40%, at least about 50%, at least about 60%, at least about 70%, at least about 80%, at least about 90%, at least about 100%, at least about 150%, at least about 200% or more relative to survival of the patient when a vector of the disclosure is administered in the absence of the contrast agent.

The disclosure also provides treatment method embodiments wherein the intrathecal administration of a vector of the disclosure and a contrast agent to the central nervous system of a patient in need thereof who is put in the Trendelenberg position results in a further increase in survival of the patient relative to survival of the patient when a vector of the disclosure is administered in the absence of the contrast agent and the Trendelenberg position. In various embodiments, administration of a vector of the disclosure and a contrast agent to the central nervous system of a patient in need thereof put in the Trendelberg position results in an increase of survival of the patient of at least about 1%, at least about 5%, at least about 10%, at least about 20%, at least about 30%, at least about 40%, at least about 50%, at least about 60%, at least about 70%, at least about 80%, at least about 90%, at least about 100%, at least about 150%, at least about 200% or more relative to survival of the patient when a vector of the disclosure is administered in the absence of the contrast agent and the Trendelenberg position.

EXAMPLES

The present invention is illustrated by the following.
Proof of concept studies in female and male Rett mouse models show therapeutic efficacy following intravenous injection of scAAV9.738.Mecp2. (Example 1)
A second generation gene therapy vector, AVXS-201, shows extension of survival over a wide range of doses following intracerebroventricular (ICV) treatment of Mecp2−/y mice. The maximal increase in median survival was 477% following AVXS-201 treatment. (Example 2)
Male Mecp2−/y mice treated with AVXS-201 show a durable improvement in behavior as measured by a composite rating developed for Rett mice. (Example 3)
Phenotypic benefit in Mecp2−/y mice treated with AVXS-201 is obtained with moderate levels of protein expression. (Example 4)
Treatment of wild type mice with AVXS-201 was well tolerated across all doses tested with consistent changes in behavioral scoring only noted in the high dose group. (Example 5 and Example 6)
Intrathecal dosing in non-human primates indicates AVXS-201 is safe and well tolerated through 18 months post injection. (Example 7)
AVXS-201 expresses transgene at physiological levels broadly in non-human primate brain and spinal cord following a one-time intrathecal injection. (Example 8)

Example 1

Gene Therapy for Rett Syndrome Proof of Concept Studies in Female Rett Mice

As proof of concept, symptomatic male and female Rett mice were intravenously treated with scAAV9.738.Mecp2 [Garg et al., *The Journal of Neuroscience: The Official Journal of the Society for Neuroscience*, 33: 13612-13620 (2013)]. The recombinant viral genome of scAAV9.738.Mecp2 (SEQ ID NO: 5) includes a 738 bp promoter fragment from the mouse Mecp2 gene [Adachi et al., *Human Molecular Genetics*, 14: 3709-3722 (2005)] driving expression of a mouse Mecp2a cDNA (CCDS Database #CCDS41016.1) and a bovine growth hormone polyadenylation signal. The gene cassette (nucleotides 198-2890 of SEQ ID NO: 5) is flanked by a mutant AAV2 inverted terminal repeat (ITR) and a wild type AAV2 ITR that enable packaging of self-complementary AAV genomes.

Self-complementary AAV9 (scAAV9) was produced by transient transfection procedures using a double-stranded AAV2-ITR-based vector, with a plasmid encoding Rep2Cap9 sequence as previously described [Gao et al., *J. Virol.*, 78: 6381-6388 (2004)] along with an adenoviral helper plasmid pHelper (Stratagene, Santa Clara, CA) in 293 cells. Virus was produced in three separate batches for the experiments and purified by two cesium chloride density gradient purification steps, dialyzed against PBS and formulated with 0.001% Pluronic-F68 to prevent virus aggregation and stored at 4° C. All vector preparations were titered by quantitative PCR using Taq-Man technology. Purity of vectors was assessed by 4-12% sodium dodecyl sulfate-acrylamide gel electrophoresis and silver staining (Invitrogen, Carlsbad, CA).

Male mice with an Mecp2 null allele were treated intravenously with $3×10^{12}$ vg of either scAAV9.738.Mecp2 or an scAAV9 control vector between 4-6 weeks of age. The animals were followed for survival and assessed weekly for a phenotypic score [Guy et al., *Science*, 315:1143-1147 (2007)].

Components of the phenotypic scoring from Guy et al. 2007:
A. Mobility: The mouse is observed when placed on bench, then when handled gently. 0=as wild-type. 1=reduced movement when compared to wild-type: extended freezing period when first placed on bench and longer periods spent immobile. 2=no spontaneous movement when placed on the bench; mouse can move in response to a gentle prod or a food pellet placed nearby. (Note: mice may become more active when in their own cage environment.)
B. Gait: 0=as wild-type. 1=hind legs are spread wider than wild-type when walking or running with reduced pelvic elevation, resulting in a "waddling" gait. 2=more severe abnormalities: tremor when feet are lifted, walks backwards or 'bunny hops' by lifting both rear feet at once.
C. Hindlimb clasping: Mouse observed when suspended by holding base of the tail. 0=legs splayed outwards. 1=hindlimbs are drawn towards each other (without touching) or one leg is drawn in to the body. 2=both legs are pulled in tightly, either touching each other or touching the body.
D. Tremor: Mouse observed while standing on the flat palm of the hand. 0=no tremor. 1=intermittent mild tremor. 2*=continuous tremor or intermittent violent tremor
E. Breathing: Movement of flanks observed while animal is standing still. 0=normal breathing. 1=periods of regular breathing interspersed with short periods of more rapid breathing or with pauses in breathing. 2*=very irregular breathing—gasping or panting.
F. General condition: Mouse observed for indicators of general well-being such as coat condition, eyes, body stance. 0=clean shiny coat, clear eyes, normal stance. 1=eyes dull, coat dull/ungroomed, somewhat hunched stance. 2*=eyes crusted or narrowed, piloerection, hunched posture.

Figure 4:
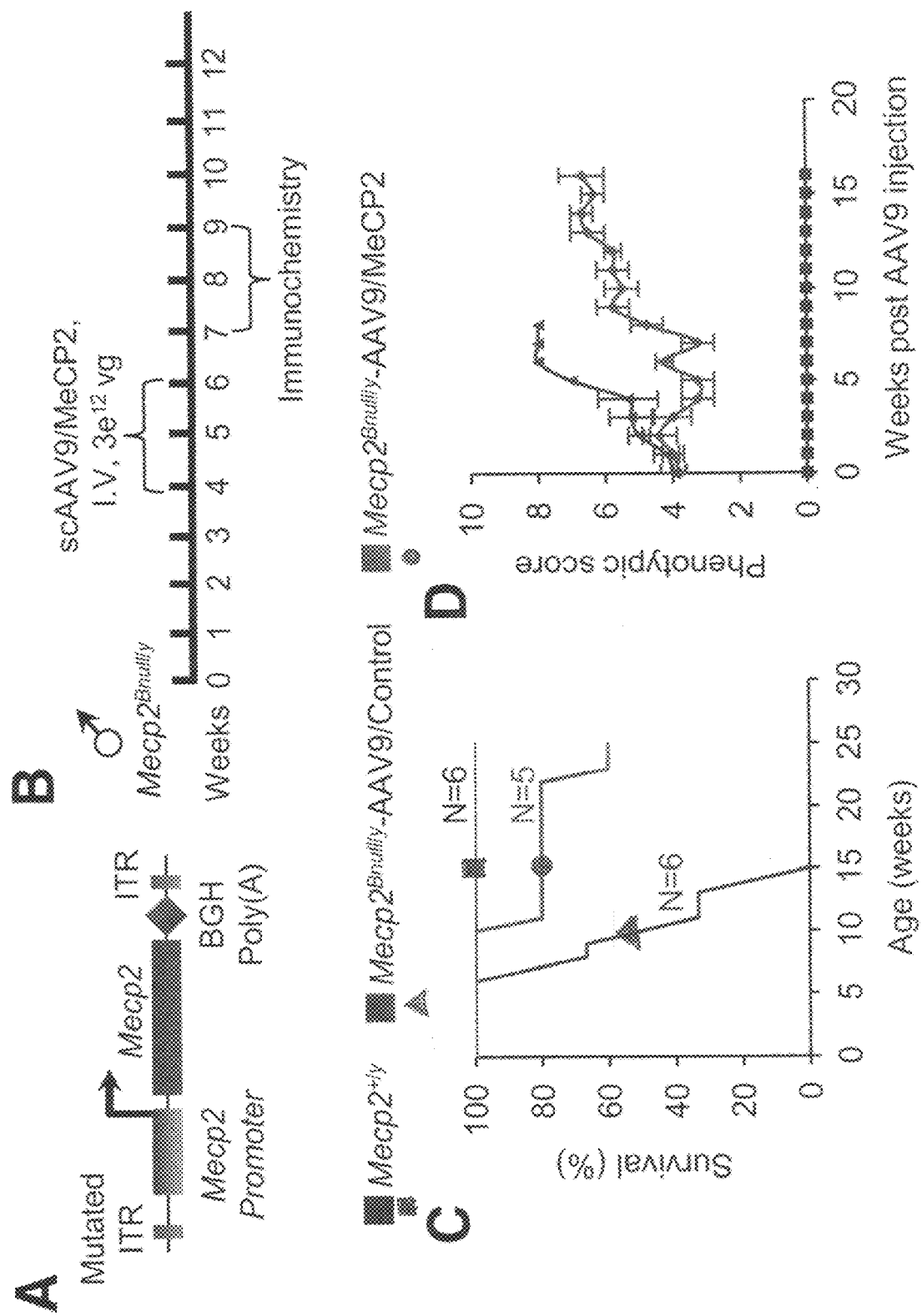
FIG. 4: Proof of concept with AAV9 mediated restoration of Mecp2 expression in male Rett mice. A) Cartoon of the recombinant AAV genome. B) Experimental design. C) Kaplan-Meier survival curve showing the increased survival of scAAV9.738.Mecp2 treated Rett mice compared to animals treated with control vector. D) Vector mediated Mecp2 restoration improves the behavioral phenotype when measured by the Bird scoring (Box 1).
Figure 5:
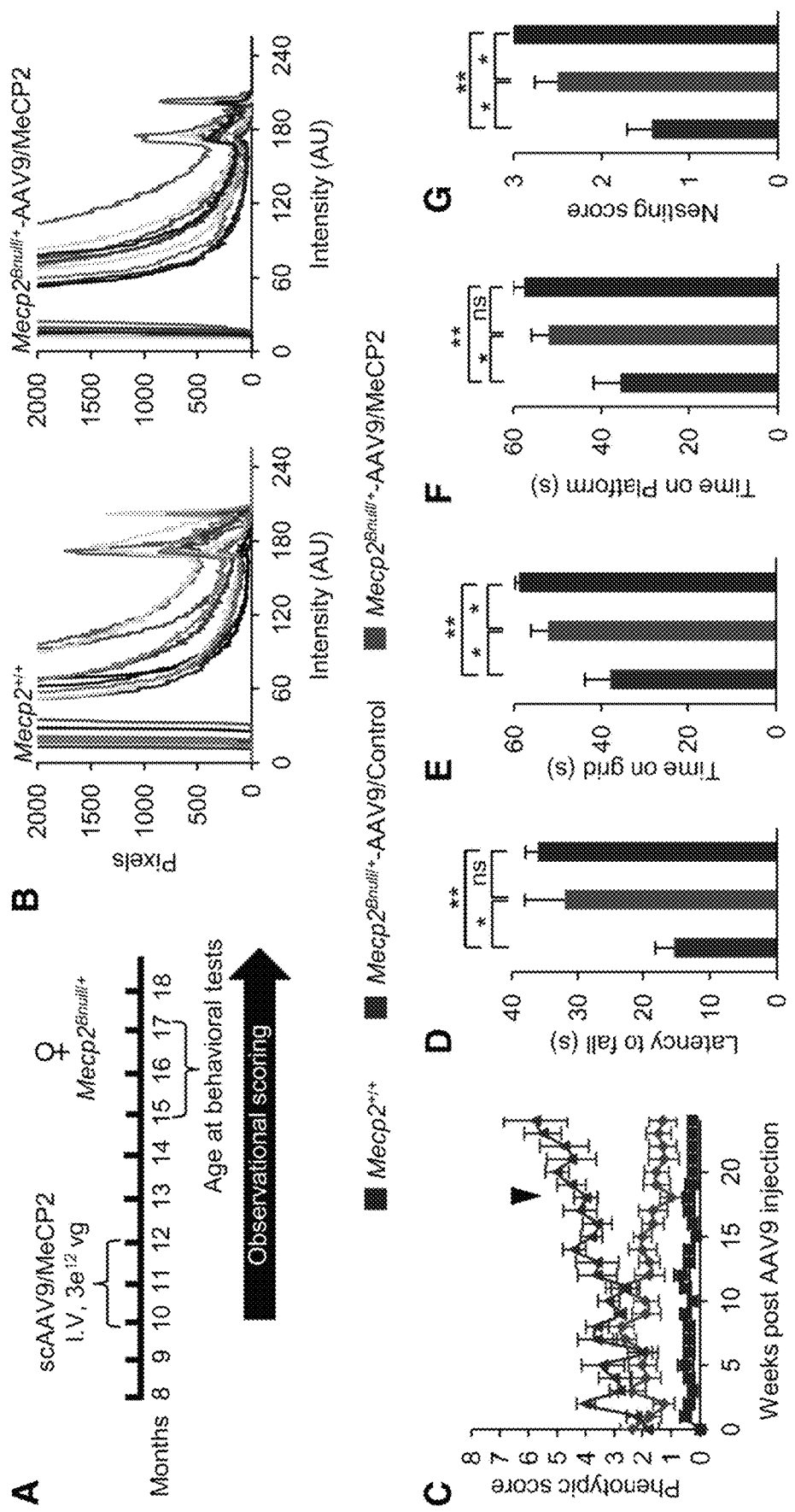
FIG. 5: scAAV9.738.Mecp2 treatment of female Rett mice makes physiological levels of Mecp2 and improves aberrant behavior. A) Experimental design B) Fluorescence intensity measurements from brain sections that were immunolabled for Mecp2 from wild type and scAAV9.738.Mecp2 treated Rett mice. The distribution of intensity measurements is similar between the two groups. C) Bird phenotype scoring shows a reduction in symptoms in animals receiving scAAV9.738.Mecp2. D-G) Rotarod, Inverted Grid, Platform and nesting behavioral assessments, respectively, all show improvement in scAAV9.738.Mecp2 treated versus control treated animals.

FIG. 4 shows that the group treated with scAAV9.738.Mecp2 did not reach median survival during the time of the experiment but surpassed control treated animals by more than 10 weeks at the time of publication. Animals treated with scAAV9.738.Mecp2 also had lower behavioral score compared to control treated animals. The experiment was repeated with affected female mice (FIG. 5). Animals were IV treated with either scAAV9.738.Mecp2 or control as before with the males. Females were treated between 10-12 months of age when Rett mice are symptomatic. Animals were followed for approximately 6 months post injection and tested for their phenotypic score. Importantly, female Rett mice do not have early lethality like the more severe males [Guy et al., Nature Genetics, 27: 322-326 (2001)]. Treatment with scAAV9.738.Mecp2 halted progression of disease and indicated a reversal of disease severity with scores retreating to near 1. This was in stark contrast to control treated animals who finished the experiment with phenotypic scores near 6 indicating a worsening of symptoms (FIG. 5C). Data from rotarod, inverted screen test, platform test and nesting ability all support behavioral improvement in animals treated with scAAV9.738.Mecp2 compared to control treated animals. Post mortem analysis of brains from scAAV9.738.Mecp2 treated females showed that the fluorescence intensity measurements of MECP2 expression mirrored that of wild type brains indicating that the gene therapy transgene expression was at approximately physiological levels.

Example 2

AVXS-201 Preclinical Efficacy Studies

Figure 6:
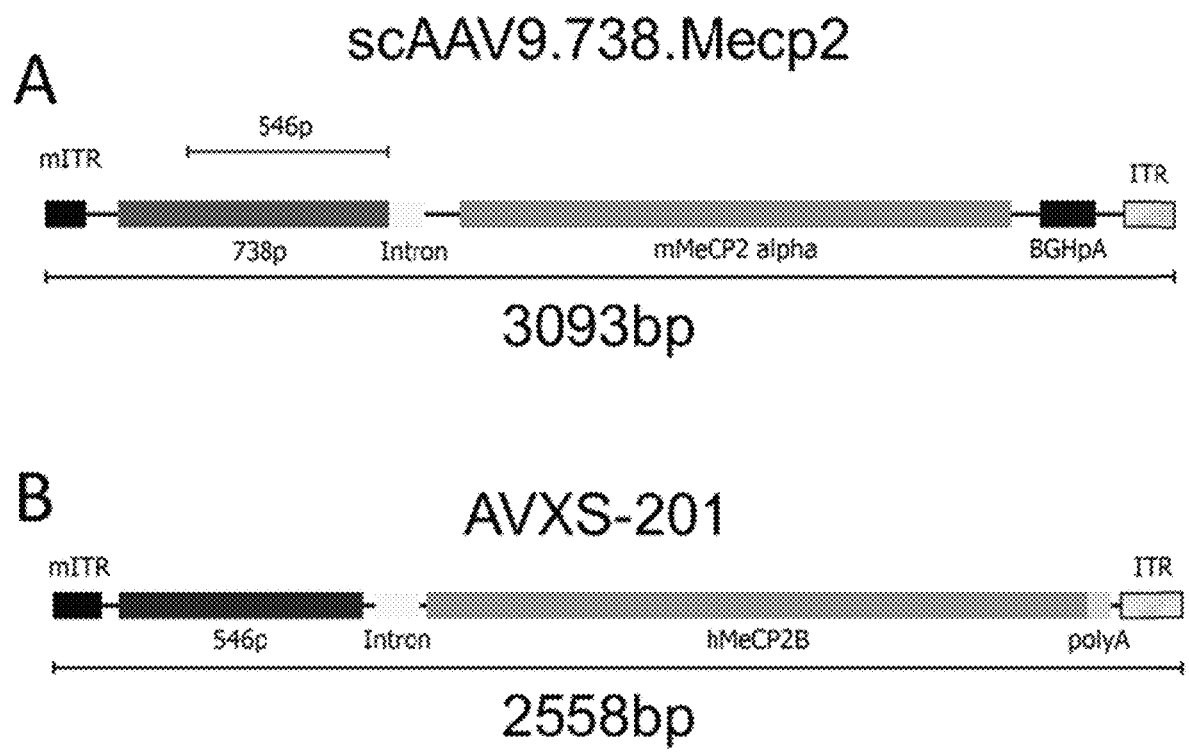
FIG. 6: A cartoon depicting the first generation (A) and the revised (B, AVXS-201) recombinant AAV genomes described here. The colors reflect similarities and differences between the constructs. Between scAAV9.738.Mecp2 and AVXS-201, the promoter was shortened, intervening sequences between key elements were shortened, the murine Mecp2 alpha cDNA was replaced with a human MECP2B cDNA, and the bovine growth hormone polyadenylation signal was changed to a shorter synthetic element. The overall goal of the changes was to improve packaging efficiency while maintaining physiological expression levels of a clinically relevant MECP2 cDNA.

To improve packaging efficiency and to incorporate a clinically relevant human MECP2 cDNA while maintaining physiological levels of gene expression, scAAV9.738.Mecp2 was re-engineered with a shorter promoter, a human MECP2B cDNA, and a synthetic polyadenylation signal. The re-engineered genome was packaged into AAV9 capsids as described below and the resulting scAAV was subsequently named "AVXS-201" (FIG. 6). AVXS-201 was originally named "AAV9-P545-MeCP2."

```
Promoter region sequence (mouse MeCP2
promoter fragment)
                                       (SEQ ID NO: 2)
GTGAACAACGCCAGGCTCCTCAACAGGCAACTTTGCTACTTCTACAGAAA

ATGATAATAAAGAAATGCTGGTGAAGTCAAATGCTTATCACAATGGTGAA

CTACTCAGCAGGGAGGCTCTAATAGGCGCCAAGAGCCTAGACTTCCTTAA

GCGCCAGAGTCCACAAGGGCCCAGTTAATCCTCAACATTCAAATGCTGCC

CACAAAACCAGCCCCTCTGTGCCCTAGCCGCCTCTTTTTTCCAAGTGACA

GTAGAACTCCACCAATCCGCAGCTGAATGGGGTCCGCCTCTTTTCCCTGC

CTAAACAGACAGGAACTCCTGCCAATTGAGGGCGTCACCGCTAAGGCTCC

GCCCCAGCCTGGGCTCCACAACCAATGAAGGGTAATCTCGACAAAGAGCA

AGGGGTGGGGCGCGGGCGCGCAGGTGCAGCAGCACACAGGCTGGTCGGGA

GGGCGGGGCGCGACGTCTGCCGTGCGGGGTCCCGGCATCGGTTGCGCGCG

CGCTCCCTCCTCTCGGAGAGAGGGCTGTGGTAAAACCCGTCCGGAAAAC

Coding region sequence (human MeCP2B cds)
                                       (SEQ ID NO: 3)
ATGGCCGCCGCCGCCGCCGCCGCGCCGAGCGGAGGAGGAGGAGGAGGCGA

GGAGGAGAGACTGGAAGAAAAGTCAGAAGACCAGGACCTCCAGGGCCTCA

AGGACAAACCCCTCAAGTTTAAAAAGGTGAAGAAAGATAAGAAAGAAGAG

AAAGAGGGCAAGCATGAGCCCGTGCAGCCATCAGCCCACCACTCTGCTGA

GCCCGCAGAGGCAGGCAAAGCAGAGACATCAGAAGGGTCAGGCTCCGCCC

CGGCTGTGCCGGAAGCTTCTGCCTCCCCCAAACAGCGGCGCTCCATCATC

CGTGACCGGGGACCCATGTATGATGACCCCACCCTGCCTGAAGGCTGGAC

ACGGAAGCTTAAGCAAAGGAAATCTGGCCGCTCTGCTGGGAAGTATGATG

TGTATTTGATCAATCCCCAGGGAAAAGCCTTTCGCTCTAAAGTGGAGTTG

ATTGCGTACTTCGAAAAGGTAGGCGACACATCCCTGGACCCTAATGATTT

TGACTTCACGGTAACTGGGAGAGGGAGCCCCTCCCGGCGAGAGCAGAAAC

CACCTAAGAAGCCCAAATCTCCCAAAGCTCCAGGAACTGGCAGAGGCCGG

GGACGCCCCAAAGGGAGCGGCACCACGAGACCCAAGGCGGCCACGTCAGA

GGGTGTGCAGGTGAAAAGGGTCCTGGAGAAAAGTCCTGGGAAGCTCCTTG

TCAAGATGCCTTTTCAAACTTCGCCAGGGGGCAAGGCTGAGGGGGGTGGG

GCCACCACATCCACCCAGGTCATGGTGATCAAACGCCCCGGCAGGAAGCG

AAAAGCTGAGGCCGACCCTCAGGCCATTCCCAAGAAACGGGGCCGAAAGC

CGGGGAGTGTGGTGGCAGCCGCTGCCGCCGAGGCCAAAAAGAAAGCCGTG

AAGGAGTCTTCTATCCGATCTGTGCAGGAGACCGTACTCCCCATCAAGAA

GCGCAAGACCCGGGAGACGGTCAGCATCGAGGTCAAGGAAGTGGTGAAGC

CCCTGCTGGTGTCCACCCTCGGTGAGAAGAGCGGGAAAGGACTGAAGACC

TGTAAGAGCCCTGGGCGGAAAAGCAAGGAGAGCAGCCCCAAGGGGCGCAG

CAGCAGCGCCTCCTCACCCCCCAAGAAGGAGCACCACCACCATCACCACC

ACTCAGAGTCCCCAAAGGCCCCCGTGCCACTGCTCCCACCCCTGCCCCCA

CCTCCACCTGAGCCCGAGAGCTCCGAGGACCCCACCAGCCCCCCTGAGCC

CCAGGACTTGAGCAGCAGCGTCTGCAAAGAGGAGAAGATGCCCAGAGGAG

GCTCACTGGAGAGCGACGGCTGCCCCAAGGAGCCAGCTAAGACTCAGCCC

GCGGTTGCCACCGCCGCCACGGCCGCAGAAAAGTACAAACACCGAGGGGA

GGGAGAGCGCAAAGACATTGTTTCATCCTCCATGCCAAGGCCAAACAGAG

AGGAGCCTGTGGACAGCCGGACGCCCGTGACCGAGAGAGTTAGCTGA

PolyA sequence (synthetic)
                                       (SEQ ID NO: 4)
AATAAAAGATCTTTATTTTCATTAGATCTGTGTGTTGGTTTTTGTGTG
``` scAAV9 was produced by transient transfection procedures using a double-stranded AAV2-ITR-based vector, with a plasmid encoding Rep2Cap9 sequence as previously described [Gao et al., supra] along with an adenoviral helper plasmid pHelper (Stratagene, Santa Clara, CA) in 293 cells. Virus was produced in three separate batches for the experiments and purified by two cesium chloride density gradient purification steps, dialyzed against PBS and formulated with 0.001% Pluronic-F68 to prevent virus aggregation and stored at 4° C. All vector preparations were titered by quantitative PCR using Taq-Man technology. Purity of vectors was assessed by 4-12% sodium dodecyl sulfate-acrylamide gel electrophoresis and silver staining (Invitrogen, Carlsbad, CA).

Figure 7:
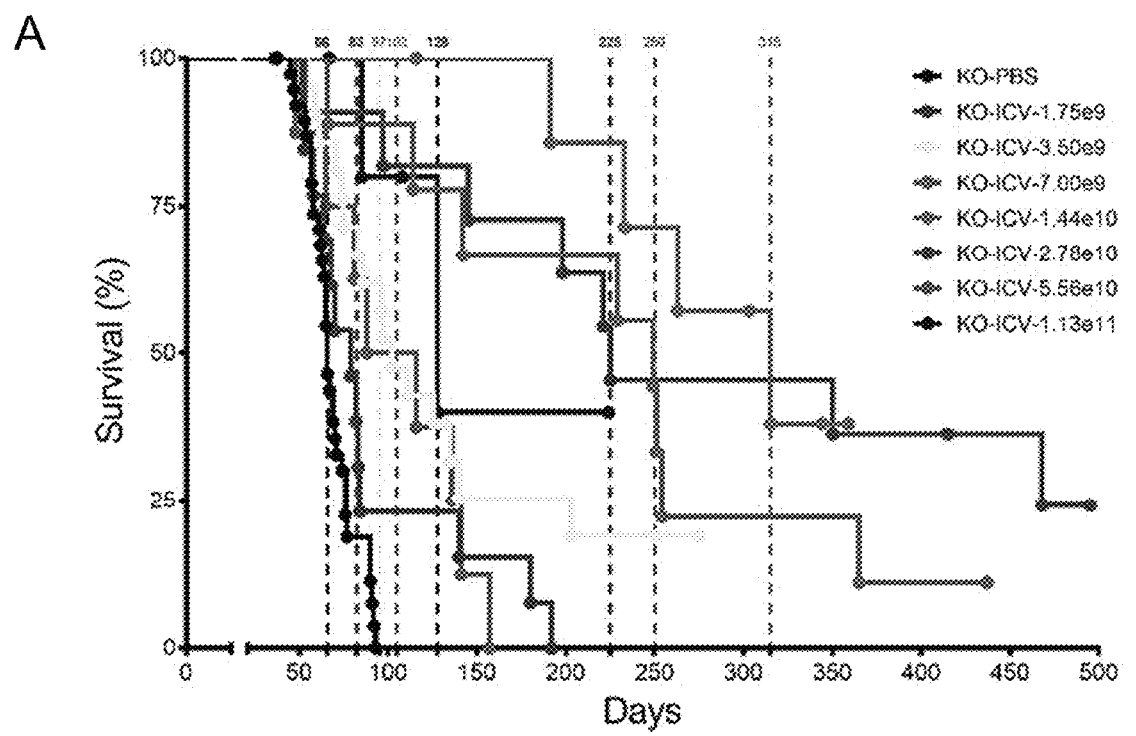
FIG. 7: Dose response of AVXS-201 in $MecpZ^{-/y}$ mice. A) A Kaplan-Meier plot of the different doses used to treat $MecpZ^{-/y}$ mice. Median survival for the dose groups are color coded and indicated by the dashed lines. Every cohort that received AVXS-201 had an increase in survival over the control treated null mice. B) The median survival data from each group were plotted to show the dose response curve. The dashed line represents median survival of PBS treated $Mecp2^{-/y}$. These data are consistent with the known effects of MECP2 deficiency and overabundance.
Figure 7:
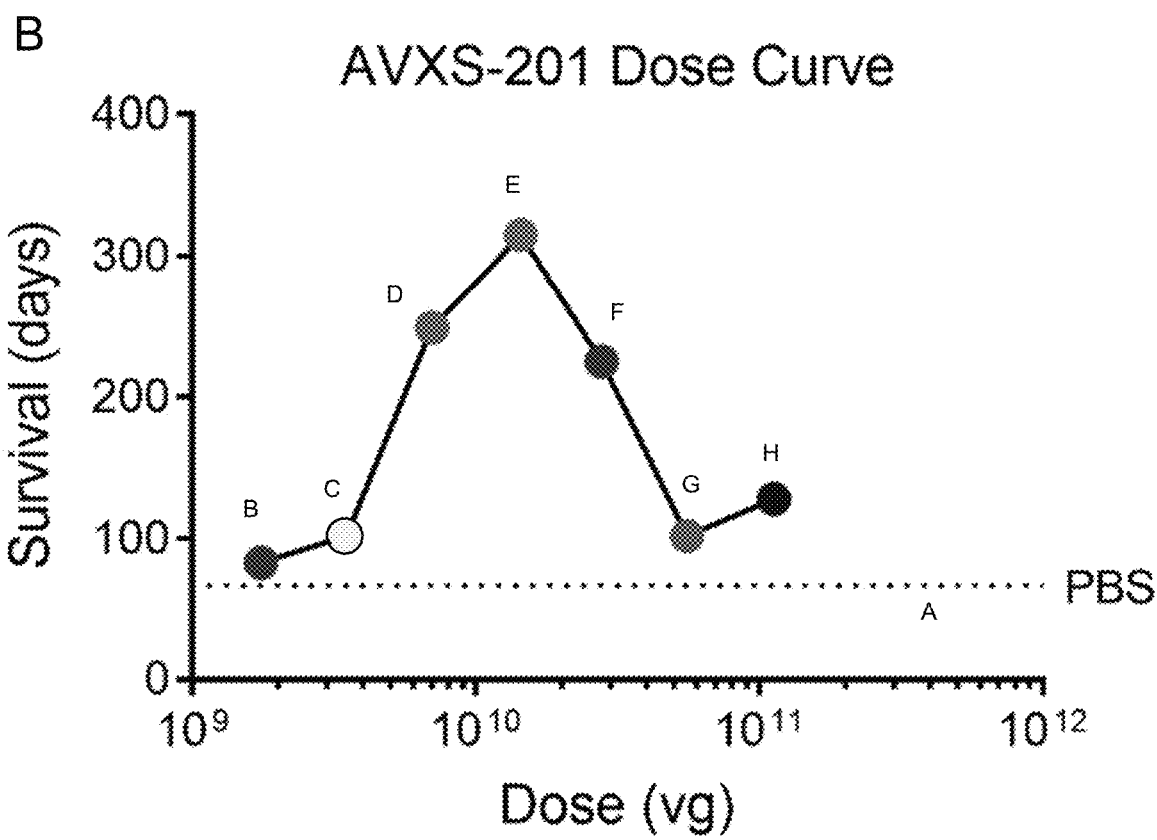

Efficacy and dosing studies were performed in the same strain of Rett mice as in FIG. 4. Doses between Example 1 and Example 2 are not compared due to improvements in titering methods. Experiments in Example 1 used optical titering of viral preparations while studies in Example 2 and below use the more accurate digital droplet PCR titer. To mimic the proposed clinical delivery route of intrathecal administration, these injections were performed as intracerebroventricular (ICV) in postnatal day 1 pups. Intrathecal delivery was chosen to deliver AVXS-201 directly to the nervous system which is the key site of action for Rett syndrome. Pups were followed for their natural lives and assessed for survival, composite phenotypic score, open field and rotarod behavior. Survival data over a two log dose range is shown in FIG. 7. The results shown in FIG. 7 demonstrate that the combination of vectors and techniques used in the treatment methods of the invention achieve an improved outcome. All doses tested extended median survival over control treated Mecp2$^{y/-}$ mice with maximum individual survival observed reaching 500 days (ongoing) compared to 93 days for control treated Rett mice. The highest median lifespan (315 d) was achieved with a moderate dose of 1.44×10$^{10}$ vg per animal. The data show a bell shaped dose response (FIG. 7B) which distinguishes the results achieved herein from the effects of improper MECP2 dosage (gene copy number) observed previously [see, for example, Lombardi et al., *The Journal of Clinical Investigation*, 125: 2914-2923 (2015)]. Importantly, even at the highest dose tested, AVXS-201 treatment did not shorten survival of Mecp$^{-/y}$ mice relative to control treatment.

Figure 8:
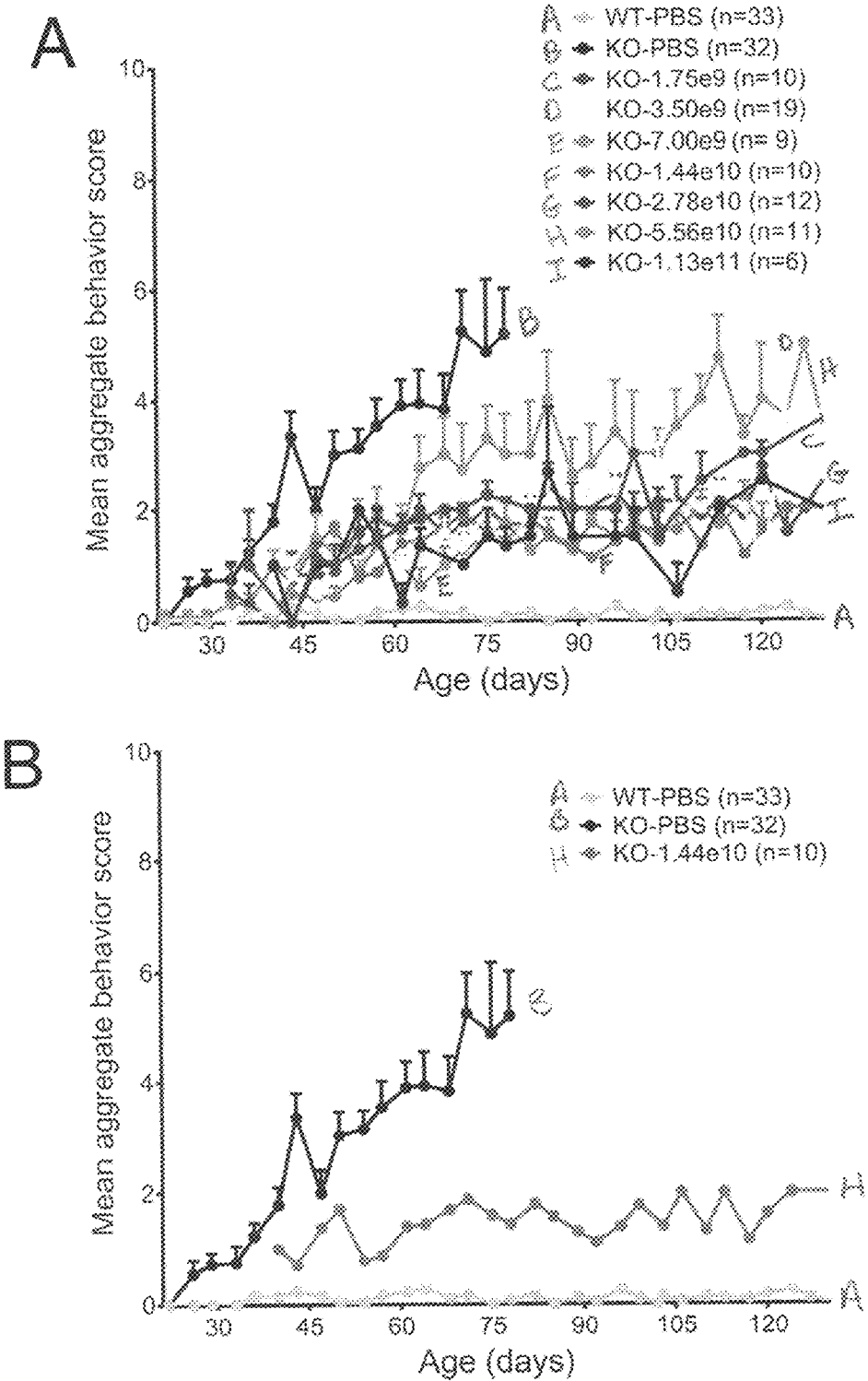
FIG. 8: Bird behavioral scoring for $MecpZ^{-/y}$ mice treated with AVXS-201. A) Control treated affected mice accumulate deficits with increasing age. Behavioral deficits are attenuated with AVXS-201 treatment regardless of dose. B) The same data as in (A) is re-graphed showing only the control treated and the AVXS-201 $1.44\times10^{10}$ vg group.
Figure 9:
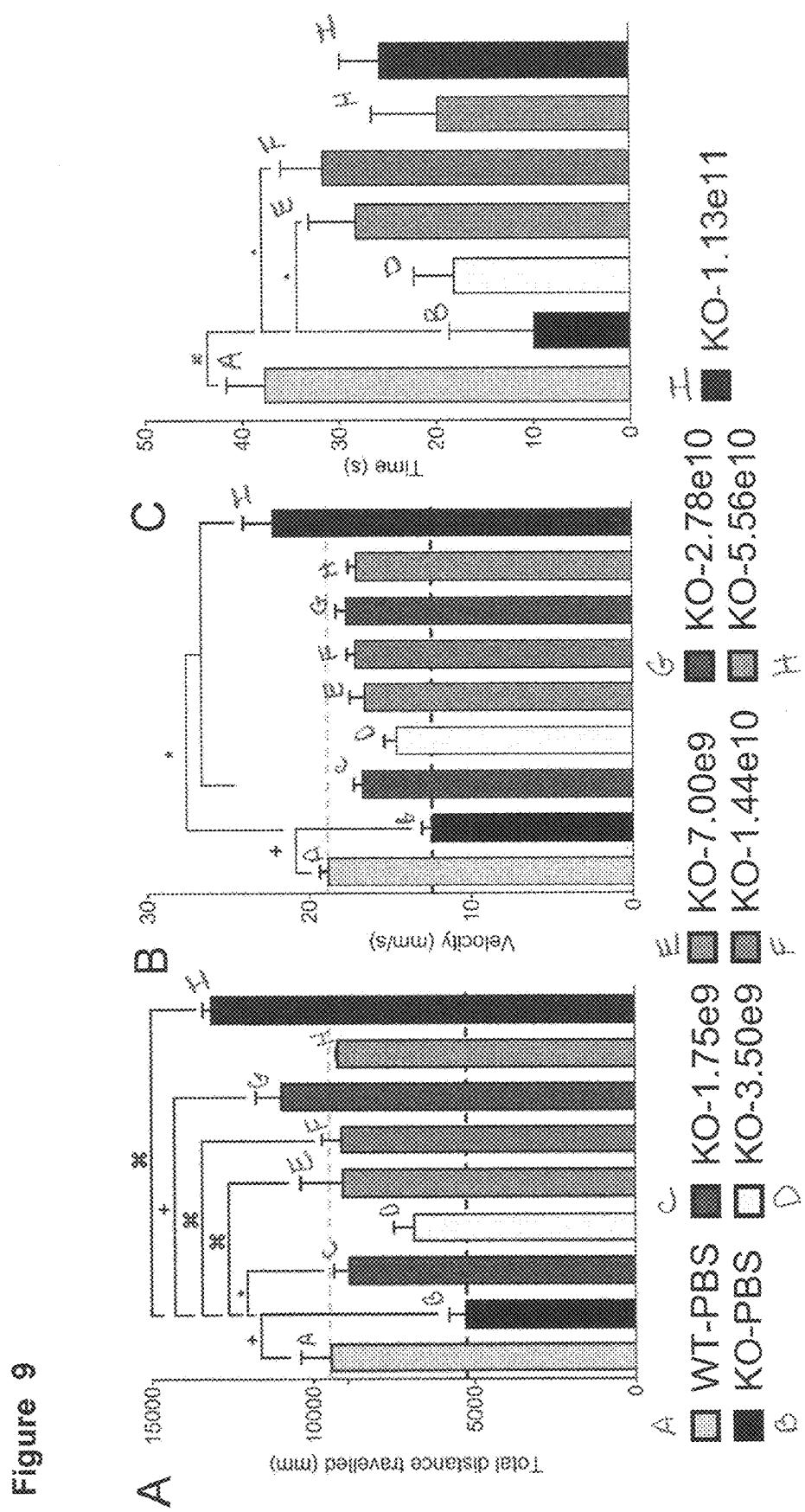
FIG. 9: AVXS-201 treated Mecp2 null mice recover spontaneous ambulation. Open field analysis shows that AVXS-201 treated null mice traverse (A) greater distances and at increased (B) average velocity compared to control treated nulls. C) Rotarod performance at 3 months of age was also improved with moderate doses of AVXS-201. $+=p\leq0.001$; $*=p\leq0.05$; $9=p\leq0.0001$.

In addition to survival, treated and control mice were scored weekly for Rett phenotypes (phenotypes set out in the previous Example). Untreated males progress rapidly from a score of 0 to an average peak of 5.25 by 10 weeks of age (FIG. 8). In contrast, phenotypic scores of all the treated groups only reached a score of about 2 by 17 weeks of age with the exception of the 5.56×10$^{10}$ vg group which reached a score of 5 at 18 weeks. Treated and control animals were also assessed in the open field and rotarod tests (FIG. 9). Reduced spontaneous movement is a symptom of Rett male mice. Open field analysis to assess spontaneous movement and velocity was performed when groups were 2-3 months of age. Affected animals had a nearly 43% reduction in the total distance traveled compared to wild type mice. Significant increases in distance traveled were noted in all but two of the groups treated with AVXS-201 over control treated Mecp2 knockout males. Velocity compared to control treated knockouts was also significantly improved. This shows that AVXS-201 treatment of a male Rett mouse model improves exploratory behavior and ambulation. Treated and control animals were tested at 3 months of age for performance on the rotarod which is a measure of motor coordination. Animals were tested on three consecutive days and scores were averaged across days and dose. The resulting data are shown in FIG. 9C. Control treated Mecp$^{-/y}$ mice performed significantly worse on rotarod compared to control treated wild type littermates. Rotarod performance was significantly improved over control treatment in the 7.00×10$^9$ and 1.44×10$^{10}$ vg cohorts.

Example 3

AVXS-201 Expression of MECP2 Protein in the Treated Rett Mouse Brain

Figure 10:
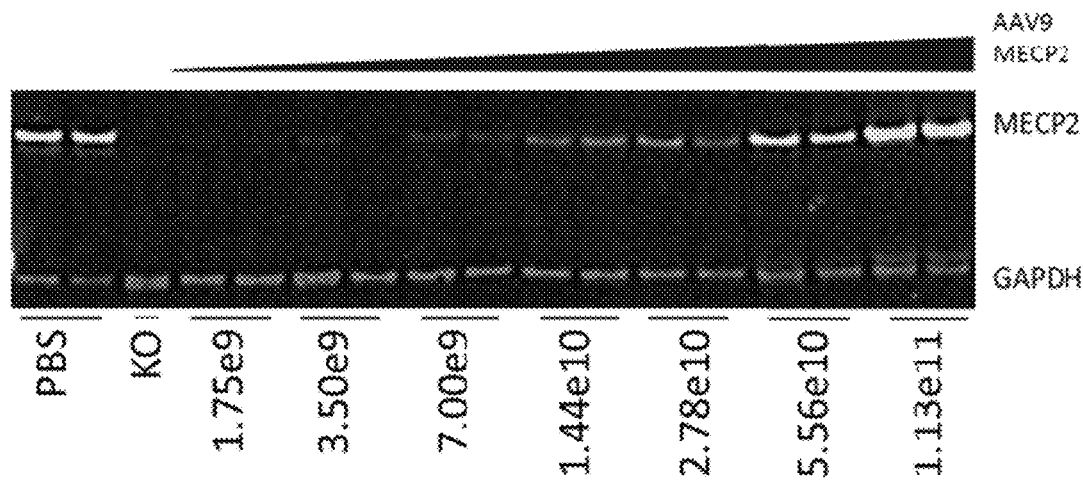
FIG. 10: AVXS-201 makes a moderate amount of MECP2 at therapeutic doses. A) Anti-MeCP2 western blots from brain hemisphere homogenates made from male wild type (PBS) or $Mecp2^{-/y}$ mice. Mecp2 nulls were either uninjected (KO) or received the indicated doses of AVXS-201. B) Quantification of panel A. The targeted therapeutic dose of $1.44\times10^{10}$ vg produced 11% of wild type levels of protein.
Figure 10:
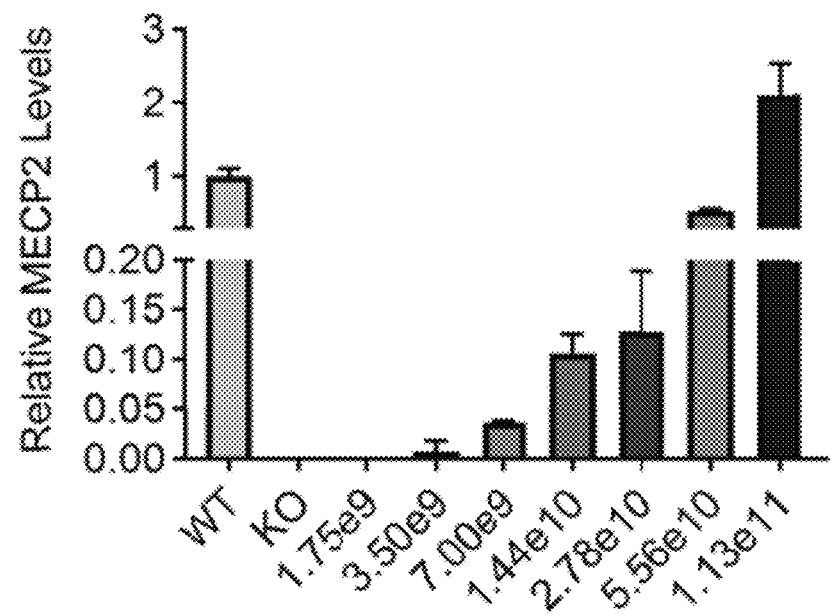

At 3 weeks post injection, PBS treated male wild type, untreated Rett and vector treated Rett animals were euthanized to examine MECP2 protein levels in the brain following postnatal day 1 ICV injection of AVXS-201. One brain hemisphere was homogenized and analyzed by western blot to monitor MECP2 expression. A representative blot and quantification are shown in FIG. 10. After normalization to the PBS treated wild type brains, the knockout and the 1.75×10$^9$ vg AVXS-201 dose group had no detectable levels of MECP2. Treatment with 3.50×10$^9$ vg and 7.00×10$^9$ vg produced detectable MECP2 levels that reached ~1% and 3.6% of wild type levels, respectively. The most effective dose when measured by increase in median survival (1.44×10$^{10}$ vg) yielded ~11% of wild type MeCP2 levels. The 5.56×10$^{10}$ vg dose examined by western blot produced MECP2 levels of ~54% of wild type while 1.13×10$^{11}$ reached more than 2× wild type levels. These data show that protein expression level and distribution throughout the brain are key for predicting the effectiveness of an MECP2 gene therapy.

Example 4

Treatment of Wild Type Mice with AVXS-201 Is Safe and Well Tolerated

An important concern for an MECP2 replacement therapy is to assess the impact on the cells expressing an intact copy of MECP2. AVXS-201 was designed with this consideration in mind by incorporating a fragment of the murine Mecp2 promoter to support physiological regulation of the MECP2 transgene. To test the safety of AVXS-201, survival and behavior analysis was performed on cohorts of wild type mice that received P1 ICV injections of AVXS-201 just as in the male Rett mice.

Figure 11:
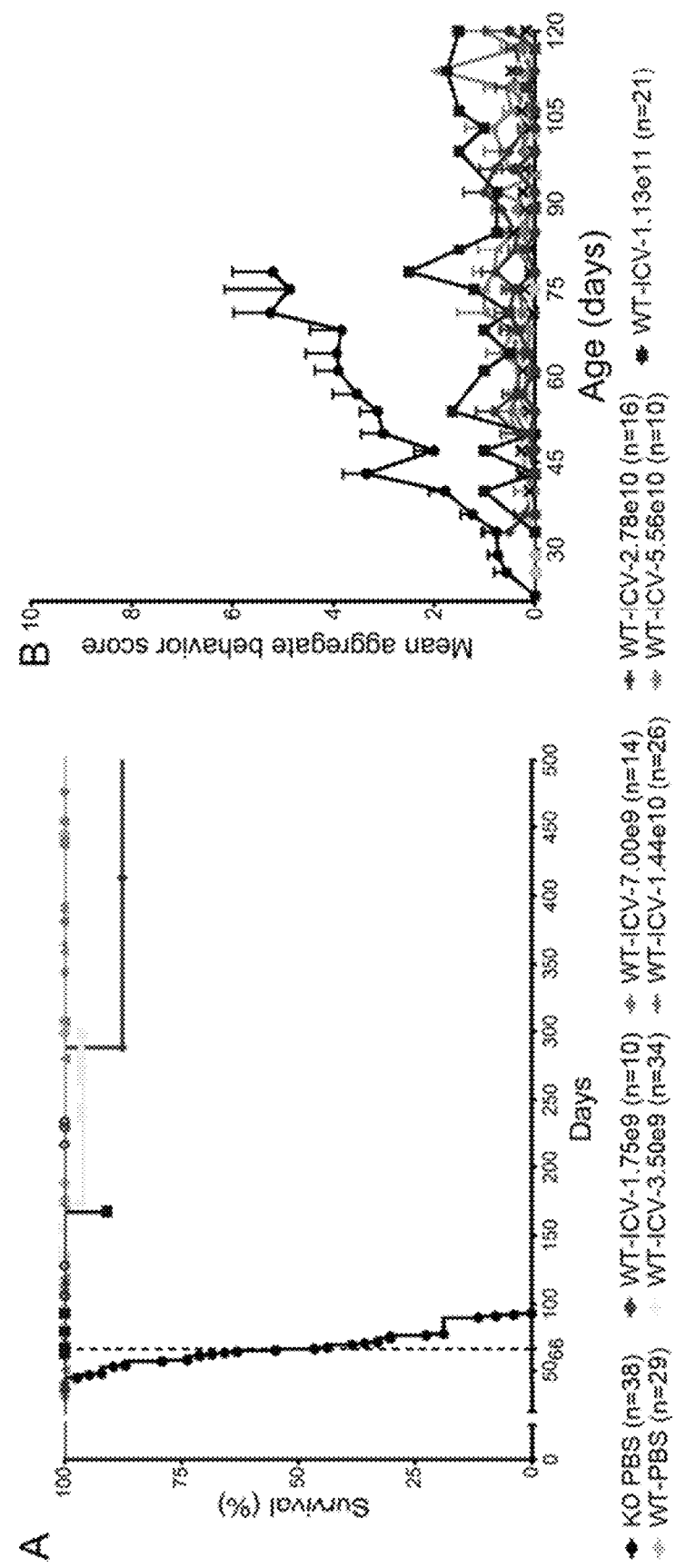
FIG. 11: AVXS-201 is well tolerated in wild type mice. A) Kaplan-Meier survival plot of male wild type mice that received P1 ICV administration of AVXS-201. B) Bird phenotypic scoring of the treated and wild type mice shows that a wide range of doses are well tolerated. The highest dose ($1.13\times10^{11}$, blue line) produced mild behavioral impairments.
Figure 12:
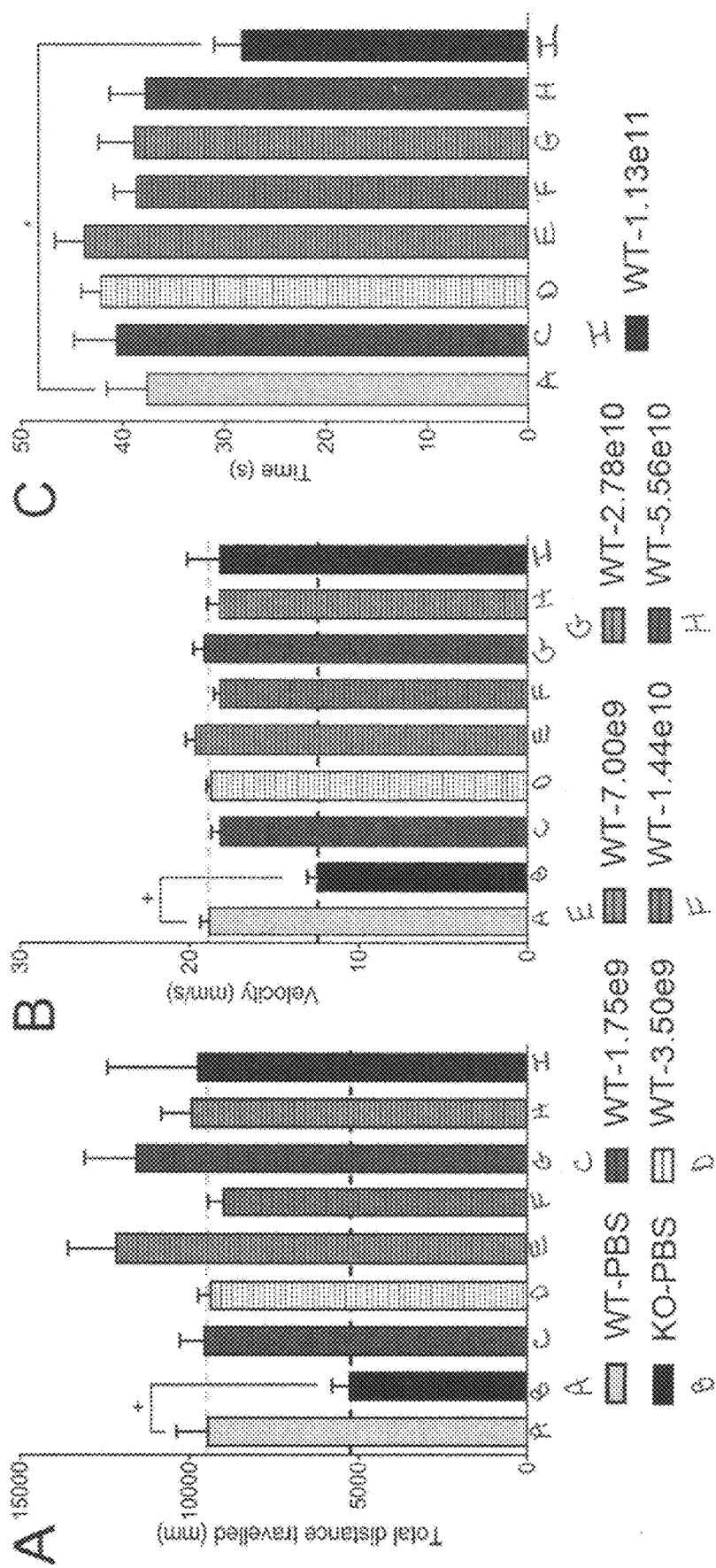
FIG. 12: AVXS-201 treatment in wild type animals does not impair ambulation. Open filed analysis of wild type male mice treated with AVXS-201 show similar (A) distances traveled and (B) average speeds as the control treated wild type mice. C) Rotarod performance was decreased in the wild type animals that received the high dose of AVXS-201. $+=p\leq0.001$, $*=p\leq0.05$

A total of 131 wild type male mice were treated with various ICV doses of AVXS-201 and followed for survival (FIG. 11). No deaths were recorded in the targeted therapeutic dose (1.44×10$^{10}$ vg) with 21 treated animals alive through P342. No deaths were recorded in the PBS treated group and one death each was recorded in the 3.50×10$^9$, 2.78×10$^{10}$ and 1.13×10$^{11}$ vg treated groups. Behavioral scoring using the criteria from Box 1, shows that vector treated groups largely had mean phenotypic scores <1. Mean aggregate scores >1 were only noted in the two highest dosed groups (5.56×10$^{10}$ and 1.13×10$^{11}$ vg). Open field testing at 2-3 months of age showed no statistical difference between vector and PBS treated wild type males (FIG. 12). Interestingly, a significant decrease in rotarod performance was detected in the 1.13×10$^{11}$ vg cohort compared to control treated wild type mice at three months of age. These data are suggestive of a toxic effect of MECP2 overexpression at the highest AVXS-201 dose. Together these data indicate that in a "worst-case scenario" of AVXS-201 treatment only transducing wild type cells, there is minimal impact on animal survival and behavior at the targeted therapeutic dose.

Example 5

Physiological Levels of MECP2 are Maintained in Brains of Wild Type Mice Treated with Therapeutic Doses of AVXS-201

Figure 13:
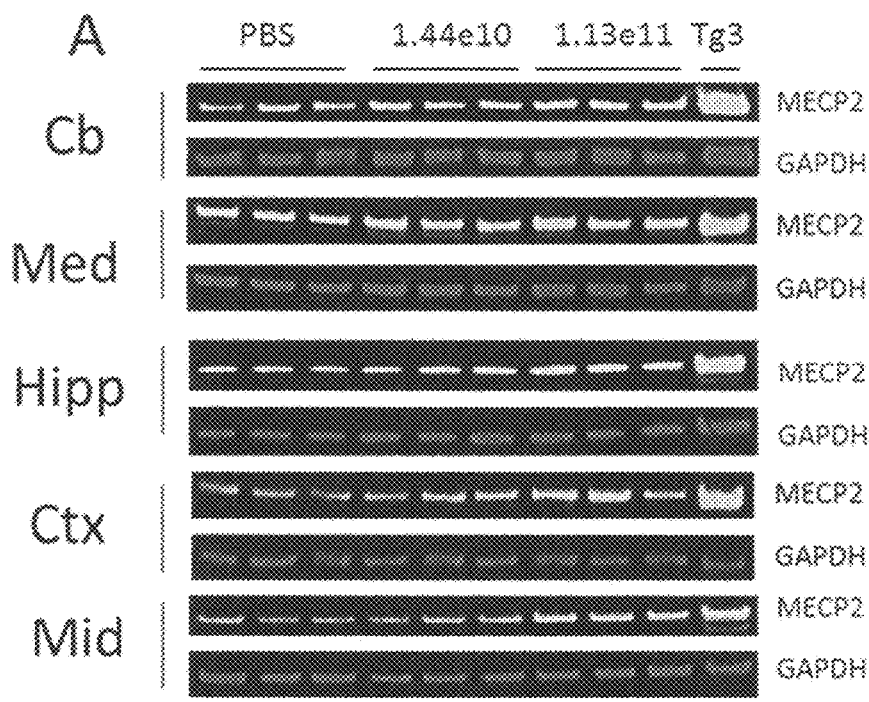
FIG. 13: AVXS-201 produces dose dependent increases in MECP2 protein in wild type brains. A) Anti-MeCP2 western blots show a dose dependent elevation of total MeCP2 protein in various brain regions 3 weeks after P1 ICV injection. (Cb=cerebellum, Med=medulla, Hipp=hippocampus, Ctx=cortex, Mid=midbrain). TG3 indicates samples taken from a severe mouse model of MeCP2 Duplication Syndrome[1]. B) Quantification of panel A. High, but not moderate, doses of AVXS-201 double MECP2 expression in select brain regions.
Figure 13:
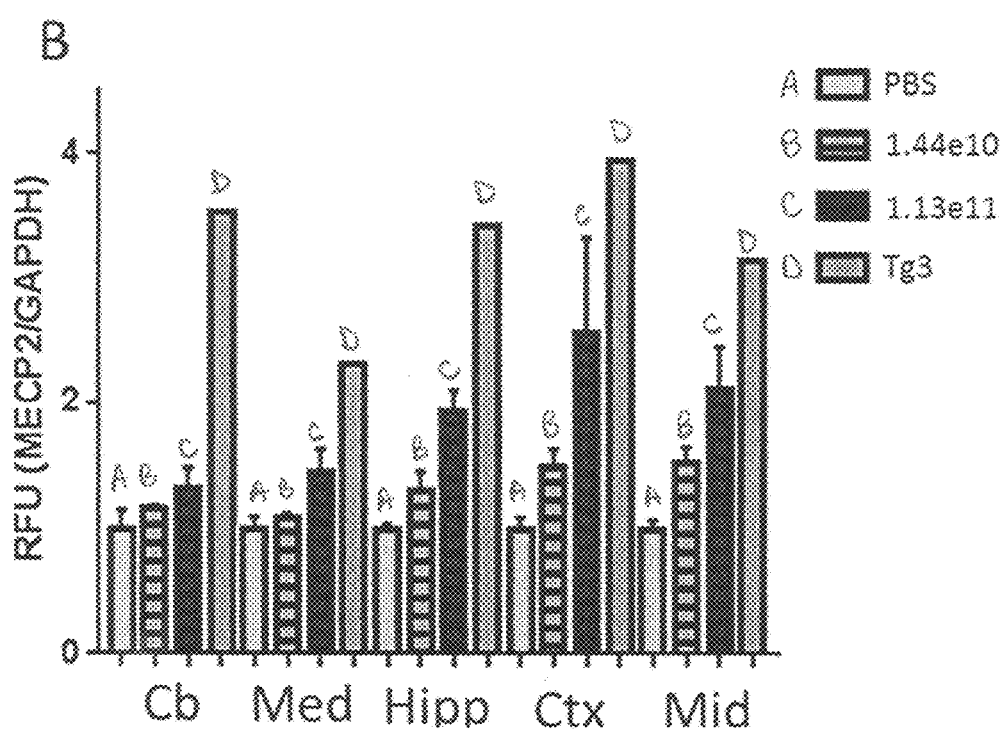

To further investigate the levels associated with symptomatic MECP2 overexpression, wild type male mice received P1 ICV injections of PBS or AVXS-201 at the therapeutic target of 1.44×10$^{10}$ vg or the highest dose tested of 1.13×10$^{11}$ vg. Animals were euthanized 3 weeks post injection, and brains were harvested for western blot. For comparison, tissues were blotted alongside brains from a mouse model of MECP2 overexpression called Tg3. Brains were dissected into separate regions (Cb=cerebellum, Med=medulla, Hipp=hippocampus, Ctx=cortex and Mid=midbrain; FIG. 13) and the individual regions were homogenized for blotting. Data was normalized to MECP2 levels in PBS treated wild type brains. Treatment with the target therapeutic dose (1.44×10$^{10}$ vg) had MECP2 levels between 1 and 1.5× wild type tissues across all regions examined. The high dose (1.13×10$^{11}$ vg) ranged from 1.31-

2.56× wild type levels, but did not reach the 2.31-3.93× levels of Tg3 tissues. These data, along with behavior and survival data shown earlier, give confidence that AVXS-201 expresses protein at near physiological levels when administered at the targeted dose. Importantly, therapeutic dosing dose not approach the 2× protein levels associated with MECP2 duplication syndrome. This shows the safety of an MECP2 replacement approach using gene therapy.

Example 6

Body Weight, Hematology and Serum Chemistry are Unremarkable in Non-Human Primates through 18 Months after Intrathecal Injection of AVXS-201

To investigate the safety and tolerability of AVXS-201 and the associated intrathecal injection procedure, three treated male cynomolgus macaques were followed for 18 months post injection. Dosing parameters are shown in Table 2.

TABLE 2

|  | Animal ID | Total Viral Genomes (vg) | Body Weight at Injection (kg) | Vector Genomes/ Body Weight (vg/kg) | Duration post Tx |
|---|---|---|---|---|---|
| Hematology and Serum Chemistry | 15C34 | $6.0 \times 10^{12}$ | 1.23 | $4.9 \times 10^{12}$ | 18 mo |
|  | 15C40 | $1.4 \times 10^{13}$ | 1.79 | $7.8 \times 10^{12}$ | 18 mo |
|  | 15C48 | $1.4 \times 10^{13}$ | 1.83 | $7.7 \times 10^{12}$ | 18 mo |
| MECP2 Expression | 15C38 | $1.3 \times 10^{13}$ | 1.68 | $7.7 \times 10^{12}$ | 6 wk |
|  | 15C49 | $1.0 \times 10^{13}$ | 1.30 | $7.7 \times 10^{12}$ | 6 wk |

Figure 14:
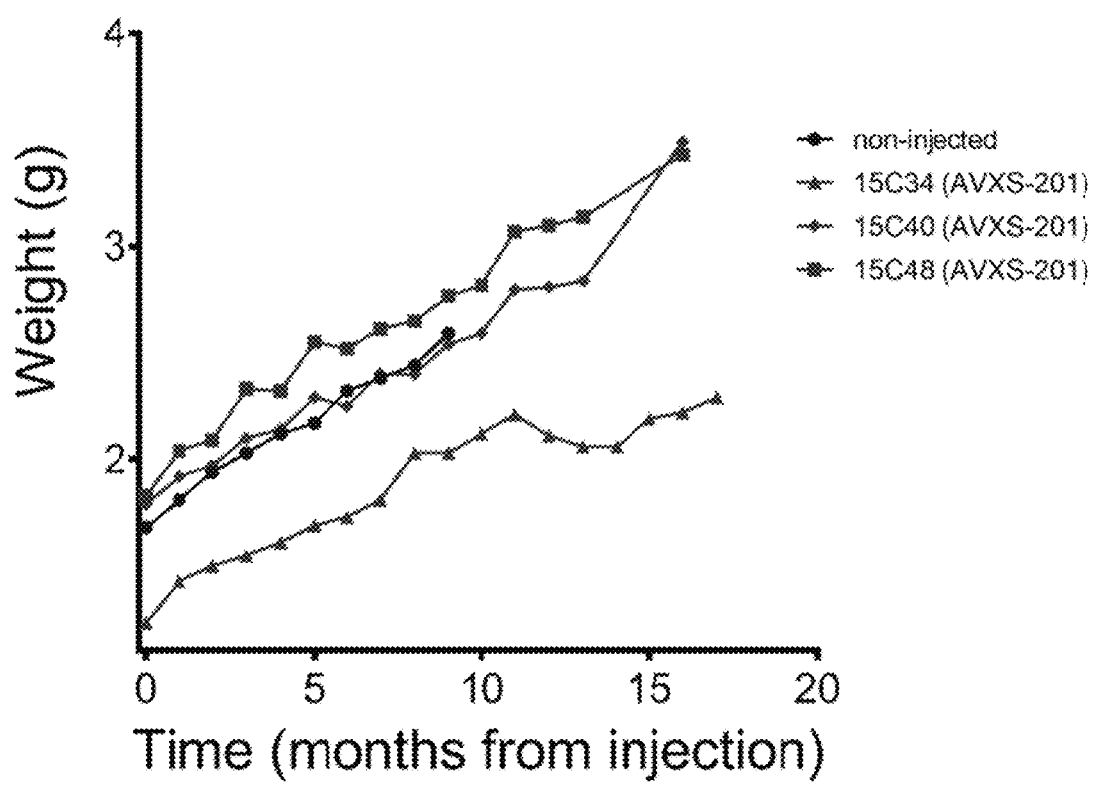
FIG. 14: Intrathecal infusion of AVXS-201 in non-human primates does not impair body weight growth. The three AVXS-201 treated animals are shown in red, and body weight for a control subject is shown in blue.
Figure 15:
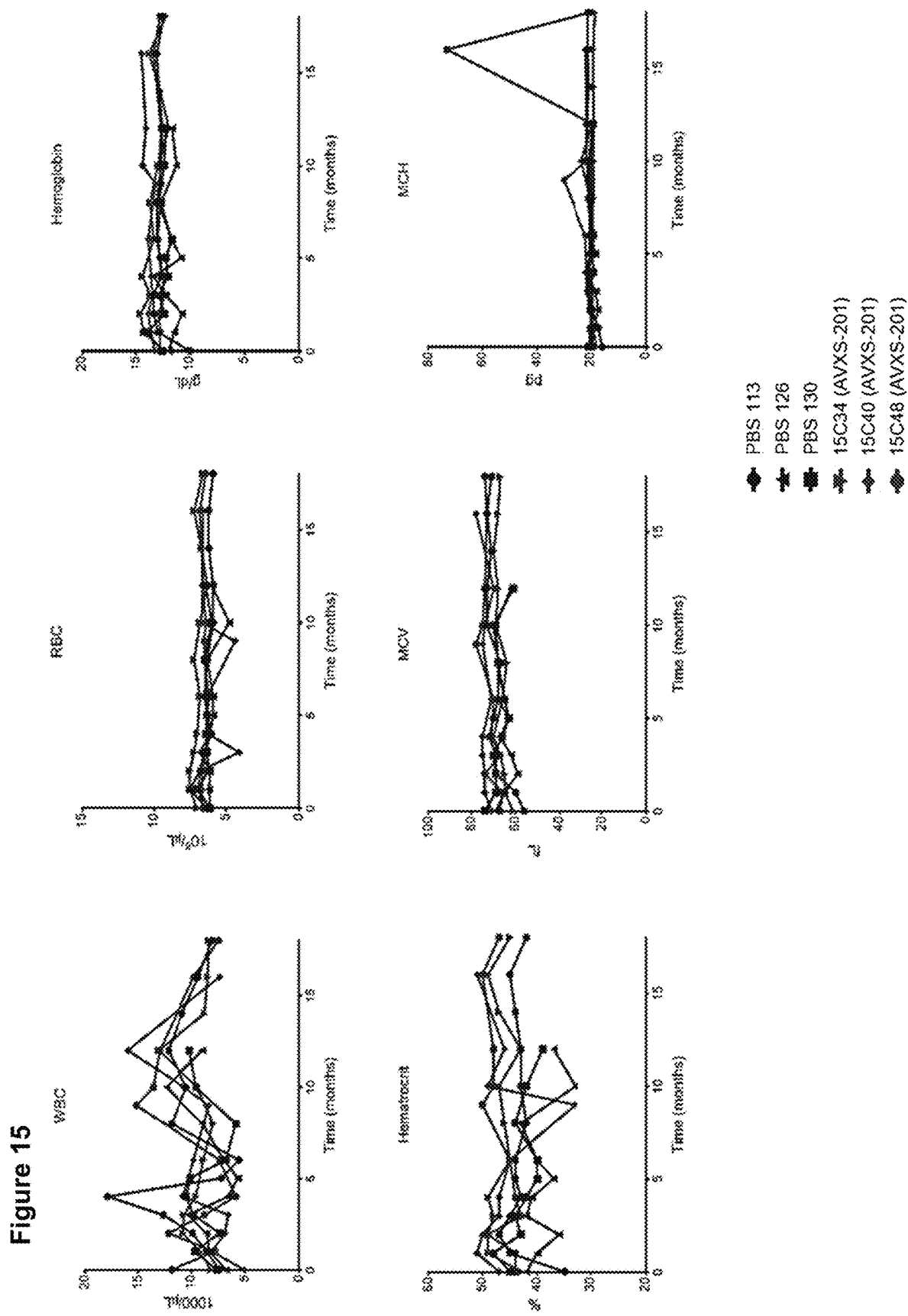
FIG. 15: Intrathecal infusion of AVXS-201 in non-human primates does not impact hematology values through 18 months post injection. Values for the three AVXS-201 treated animals are shown in red and control subjects are shown in blue.
Figure 15:
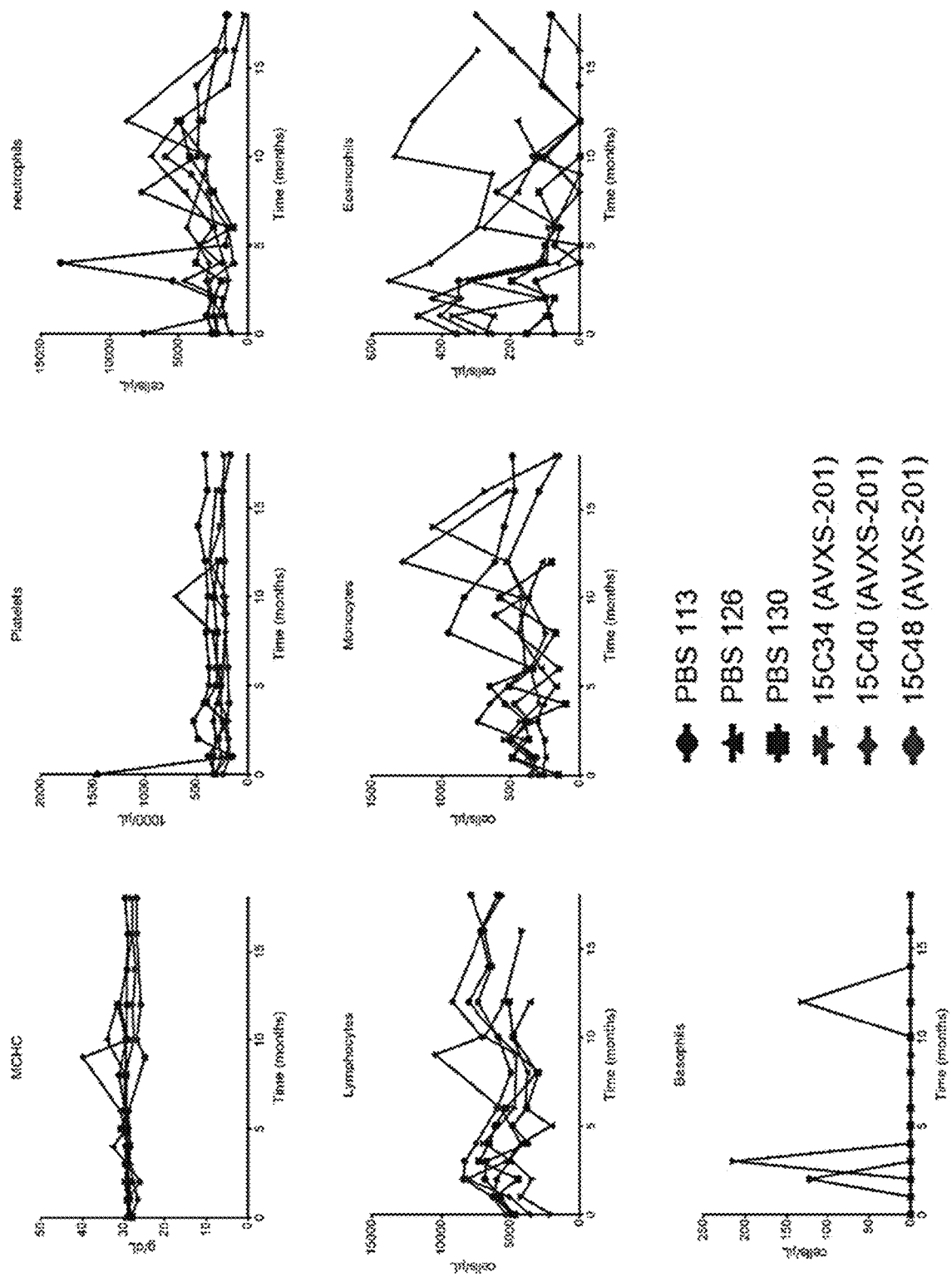
Figure 16:
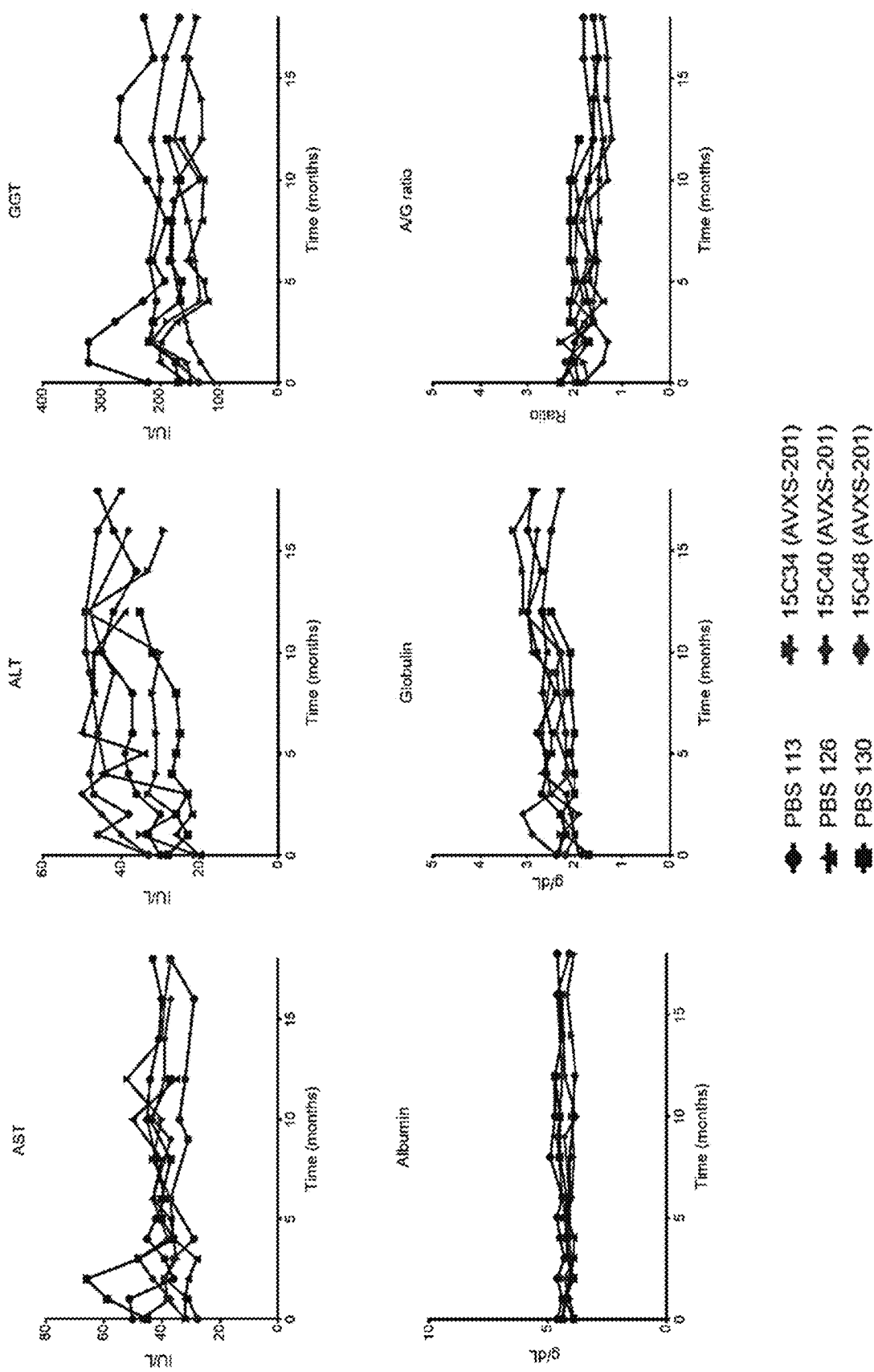
FIG. 16: Intrathecal infusion of AVXS-201 in non-human primates does not impact serum chemistry through 12-18 months post injection. Liver and electrolyte values are similar between AVXS-201 and control treated subjects. Values for the three AVXS-201 treated animals are shown in red and control subjects are shown in blue.
Figure 16:
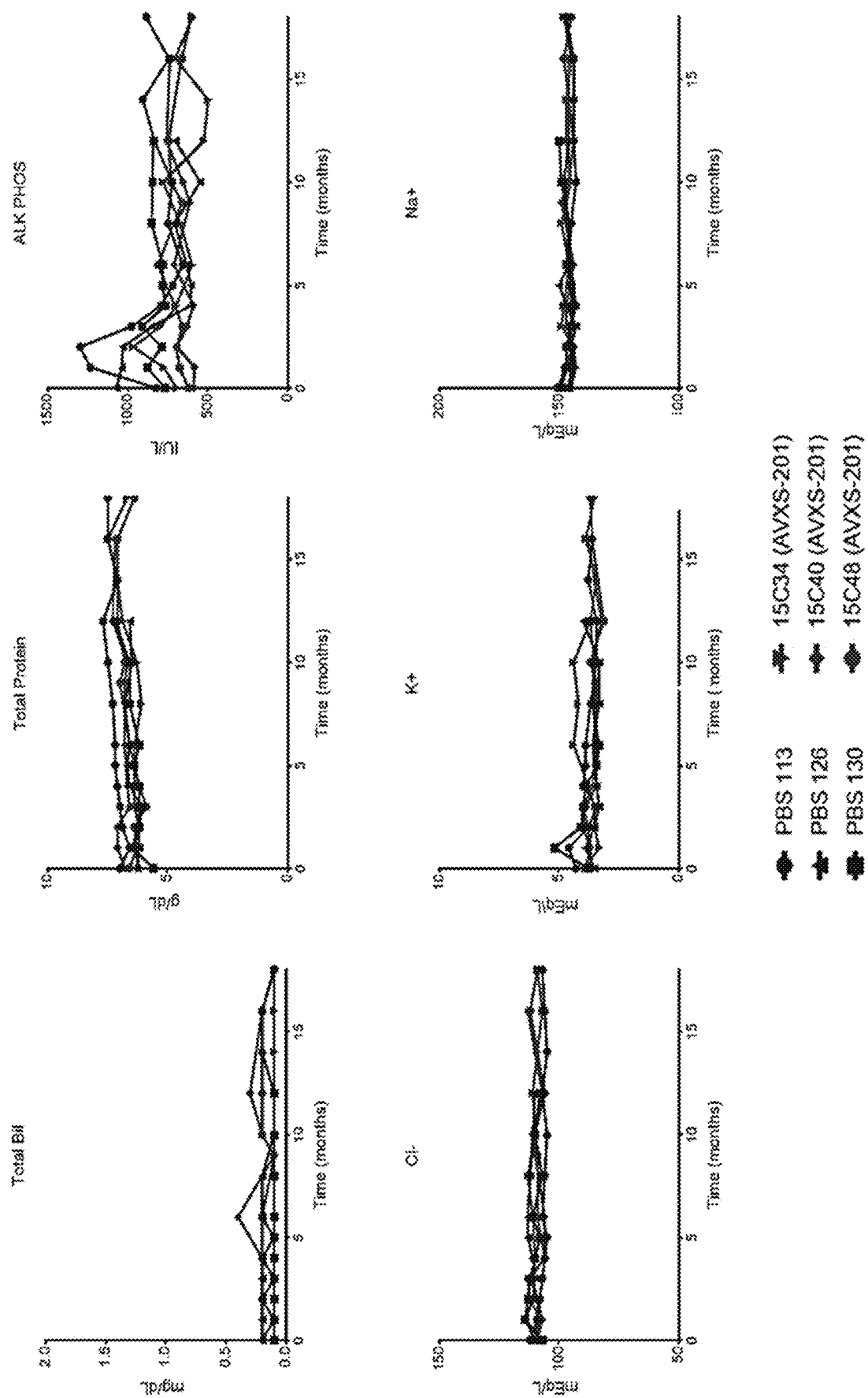
Figure 17:
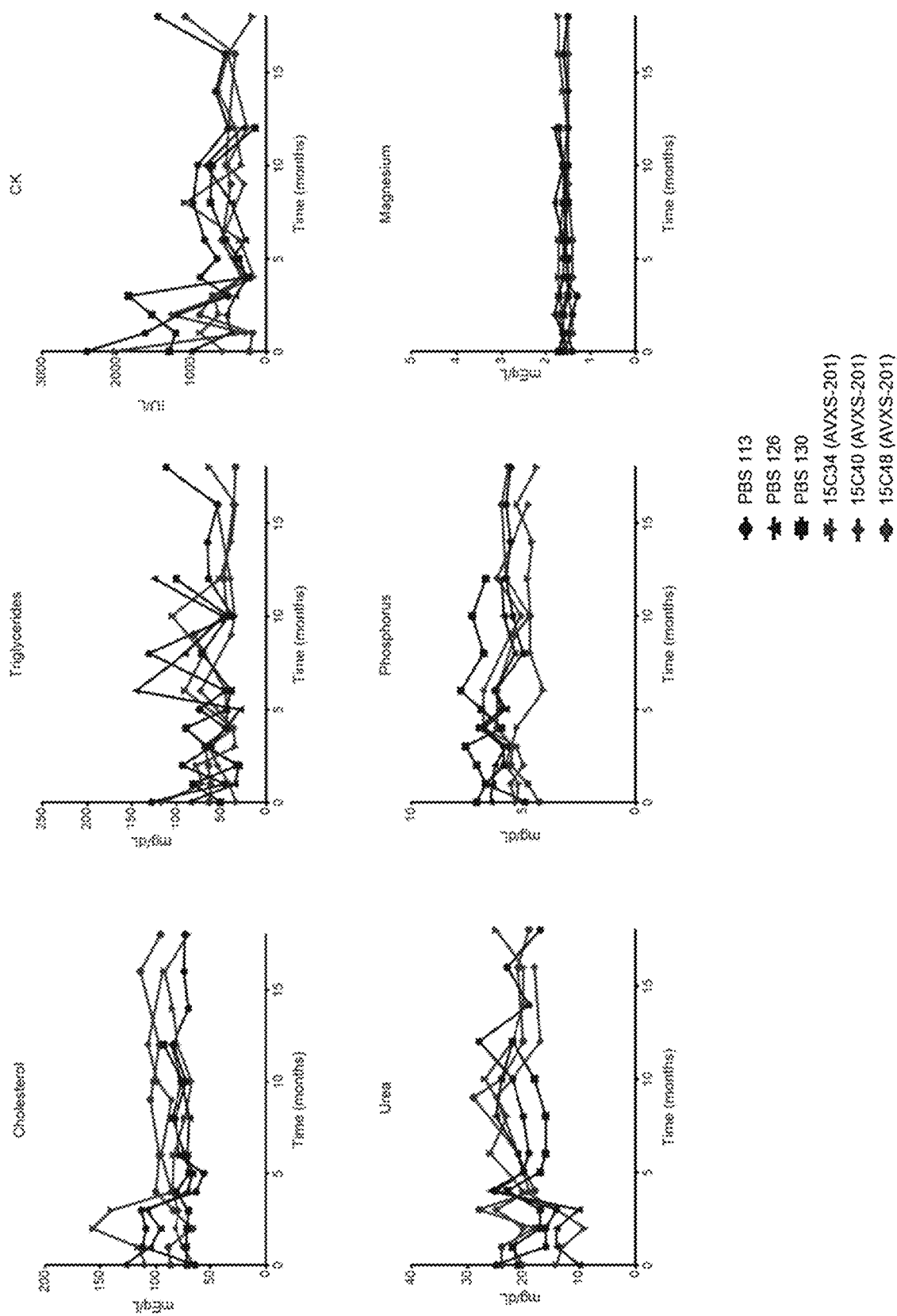
FIG. 17: Intrathecal infusion of AVXS-201 in non-human primates does not impact serum chemistry through 12-18 months post injection. Cardiac and renal values are similar between AVXS-201 and control treated subjects. Values for the three AVXS-201 treated animals are shown in red and control subjects are shown in blue.
Figure 17:
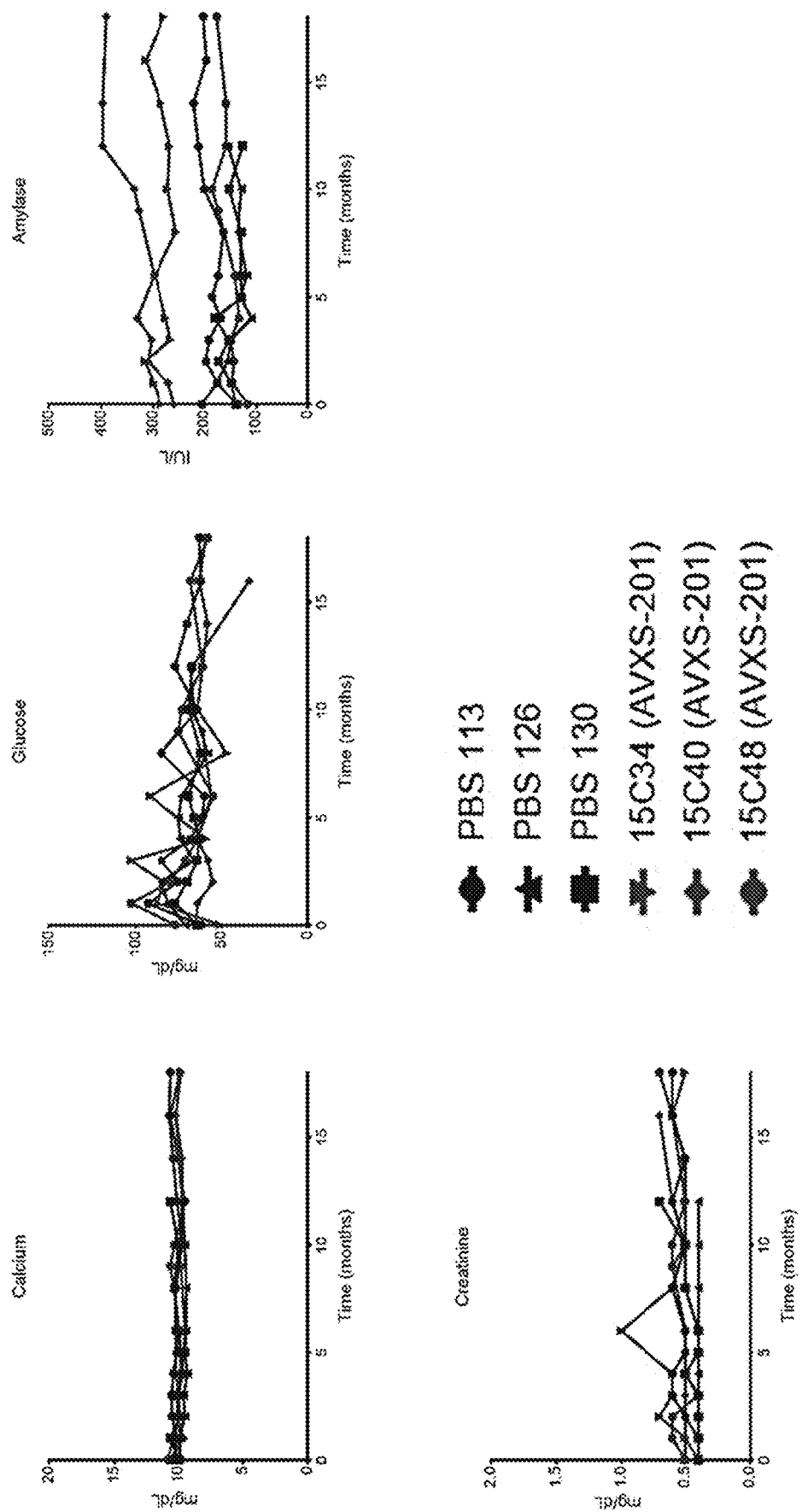

Two animals were treated at the intended therapeutic dose (~$1.44 \times 10^9$ vg equivalent on a per kg of body weight basis), and one received a ~2-fold lower dose (~$7.00 \times 10^8$ vg equivalent on a per kg of body weight basis). The intrathecal injection procedure was previously described in Meyer et al., *Molecular Therapy: The Journal of the American Society of Gene Therapy*, 23: 477-487 (2015). Briefly, vector was mixed with contrast agent for verifying vector spread. The anesthetized subject was placed in the lateral decubitus position and the posterior midline injection site at ~L4/5 level (below the conus of the spinal cord) was prepared. Under sterile conditions, a spinal needle with stylet was inserted and subarachnoid cannulation was confirmed with the flow of clear CSF from the needle. 0.8 ml of CSF was drained in order to decrease the pressure in the subarachnoid space and immediately after the vector solution was injected. Following injection, animals were kept in the Trendelenburg position and their body was tilted head-down for 10 minutes. Treated animals were dosed at 6 or 12 months of age, body weight, blood counts and serum chemistries were collected monthly for the first 6 months post injection, and every two months thereafter. Body weight is shown in FIG. 14, blood counts are shown in FIG. 15 and serum chemistries are shown in FIGS. 16 and 17 graphed with values from control treated animals from the same colony at the Mannheimer Foundation (Homestead, FL). Overall, body weight, cell counts and serum values from vector treated animals were consistent with control treated animals. No values substantially deviated from controls for more than 2 consecutive observations in a given animal with the exception of amylase which was higher in two vector treated animals at baseline. These data show that AVXS-201 and the intrathecal injection procedure are safe and well tolerated.

Example 7

Histopathological Analysis of Tissues from Non-Human Primates Following Intrathecal Injection of AVXS-201

In addition to the in vivo (Example 6) and post mortem analyses (Example 8) samples of visceral and nervous system tissues from animals 15C38, 15C49 and 15C34 (Table 1) were sent to GEMpath Inc. (Longmont, CO) for paraffin embedding, sectioning and hematoxylin and eosin staining. The remaining animals (Table 8.2) are still in life and will be sent for analysis at study conclusion. Slides were read and reports were prepared by a GEMpath Board Certified Veterinary Pathologist. The tissues sampled and examined are shown in Table 3. The pathology reports note that AVXS-201 treatment did not induce lesions in any protocol-specified tissues at the 6 week or 18 month time point.

TABLE 3

| Animal ID | Tissues |
|---|---|
| 15C38 15C49 | Adrenal Gland, Brain (amygdala, striatum, hippocampus, occipital cortex, temporal cortex, mid brain, brain stem, cerebellum), Eye and Optic Nerve, Heart, Kidney, Liver, Lung, Lymph Node (inguinal), Pancreas, Spinal Cord (sections from cervical, thoracic, lumbar and sacral regions; some sections had attached dorsal root ganglia), Small Intestine (jejunum and ileum), Skeletal Muscle (diaphragm, gastrocnemius, quadriceps femoris, triceps brachii, transverse abdominal, tibialis anterior), Spleen, Testis/Epididymis, Thymus, Urinary Bladder |
| 15C34 | Adrenal Gland, Brain (amygdala, striatum, hippocampus, hypothalamus, visual cortex, motor and somatosensory cortex, associative cortex, auditory cortex, superior and inferior colliculi, cerebellum, deep cerebellar nuclei, pons and medulla oblongata), Eye and Optic Nerve, Heart, Kidney, Liver, Lung, Lymph Node, Pancreas, Spinal Cord (sections from cervical, thoracic, lumbar and sacral regions), Small Intestine (jejunum and ileum), Skeletal Muscle (diaphragm, gastrocnemius, quadriceps femoris, triceps brachii, transverse abdominal, tibialis anterior), Spleen, Testis/Epididymis, Thymus, Urinary Bladder |

Example 8

Physiological Levels of MeCP2 in the Non-Human Primate Brain Following Intrathecal Injection of AVXS-201

Figure 18:
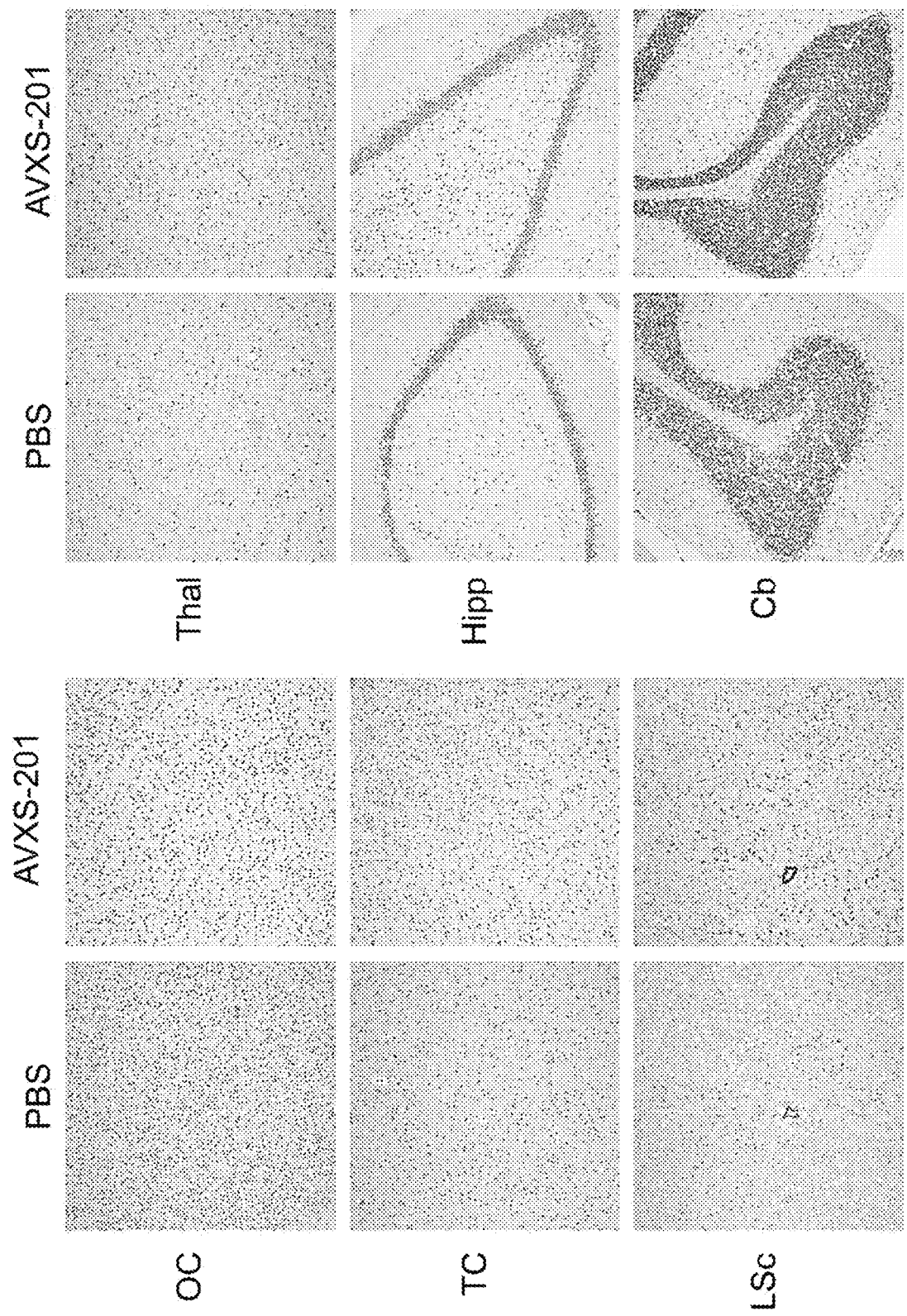
FIG. 18: Similar levels of MeCP2 expression throughout the brains of AVXS-201 treated and control non-human primates. Anti-MeCP2 immunohistochemistry revealed no gross structural abnormalities or obvious differences in MeCP2 expression. OC=Occipital Cortex, TC=Temporal Cortex, LSc=Lumbar spinal cord, Thal=Thalamus, Hipp=Hippocampus, Cb=Cerebellum.
Figure 19:
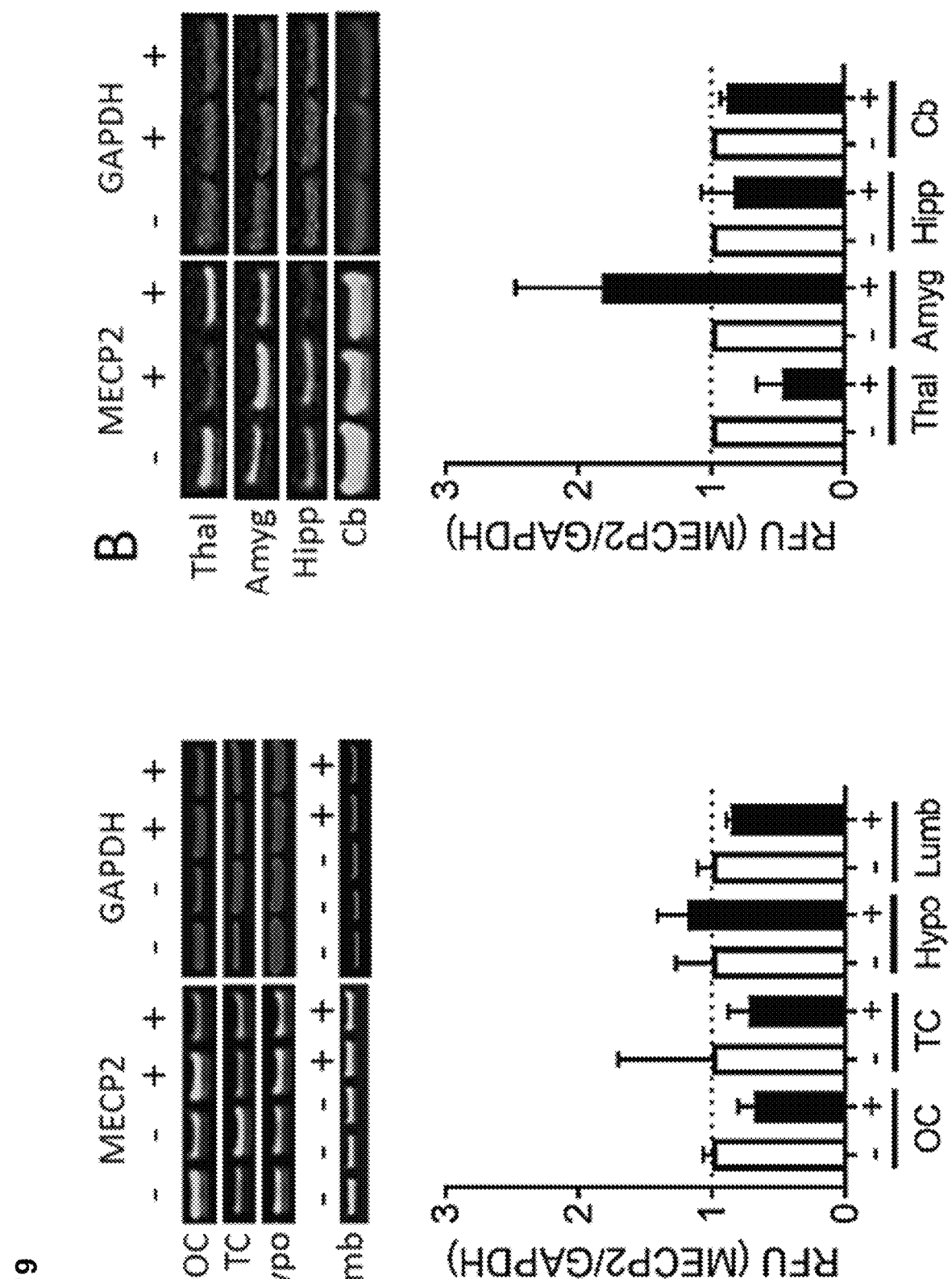
FIG. 19: Western blots of brain regions from control and AVXS-201 injected animals show similar levels of MeCP2. Total MeCP2 levels are shown in green and GAPDH loading controls are shown in red. Quantifications of panels A and B are shown below their respective blots. Dashed lines in the graphs indicate the average normalized values detected across controls. OC=Occipital Cortex, TC=Temporal Cortex, LSc=Lumbar spinal cord, Thal=Thalamus, Hipp=Hippocampus, Cb=Cerebellum. Values are shown as average±SEM.
Figure 20:
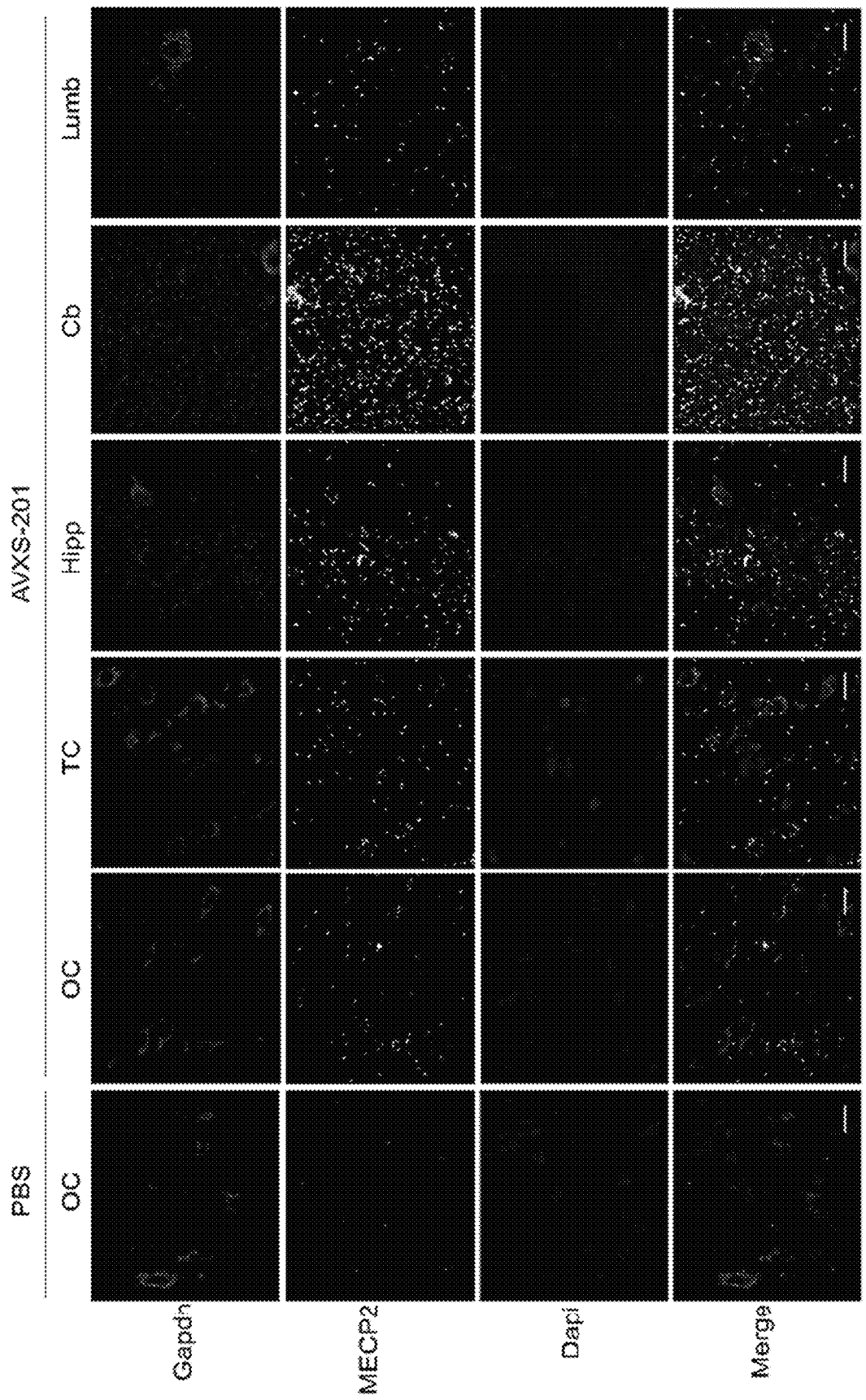
FIG. 20: In situ hybridization shows vector derived transcript in all regions examined from brains of AVXS-201 treated animals but not controls. The figure shows probes against Gapdh (red) and vector derived MECP2 mRNA (green) along with nuclear labeling (Dapi, blue). OC=Occipital Cortex, TC=Temporal Cortex, LSc=Lumbar spinal cord, Hipp=Hippocampus, Cb=Cerebellum. Scale bars=20 µm.
Figure 21:
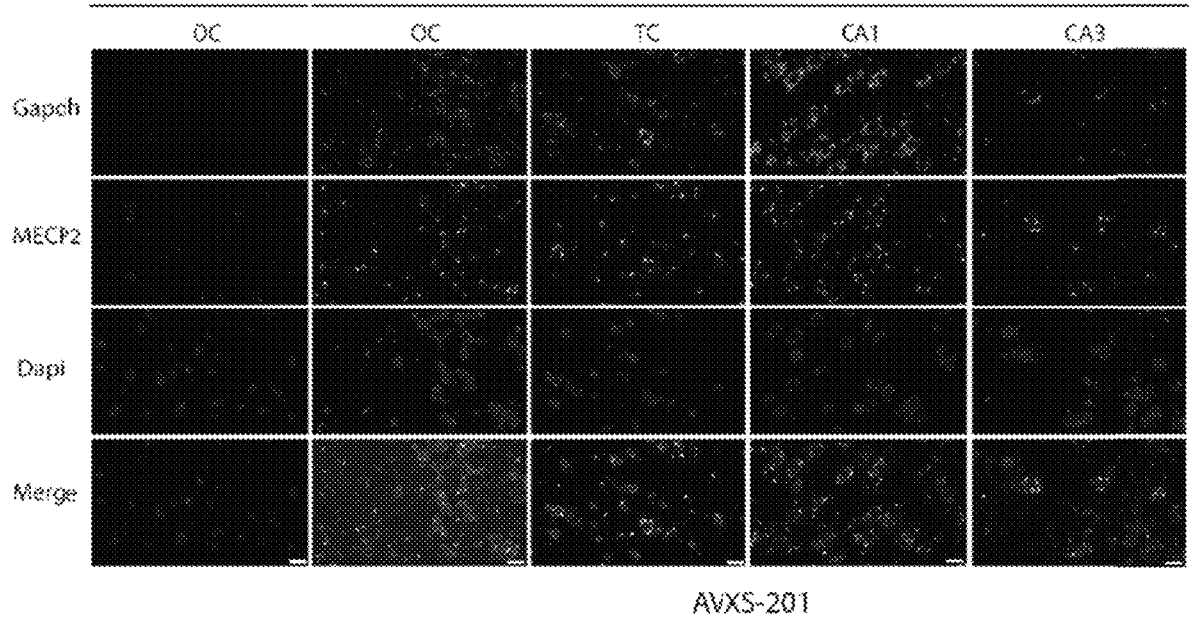
FIG. 21: In situ hybridization shows vector derived transcript in all regions examined from brains of AVXS-201 treated animals but not controls 18 months post injection. The figure shows probes against Gapdh (red) and vector derived MECP2 mRNA (green) along with nuclear labeling (Dapi, blue). OC=Occipital Cortex, TC=Temporal Cortex, CA1 and CA3=Regions of the Hippocampus, CC=Corpus Callosum, Thal=Thalamus, Cau=Caudate, Put=Putamen, SColl=Superior Colliculus, Med=Medulla, Cb=Cerebellum, Cerv=cervical spinal cord, Thor=thoracic spinal cord, Lumb=lumbar spinal cord. Scale bars=20 µm
Figure 21:
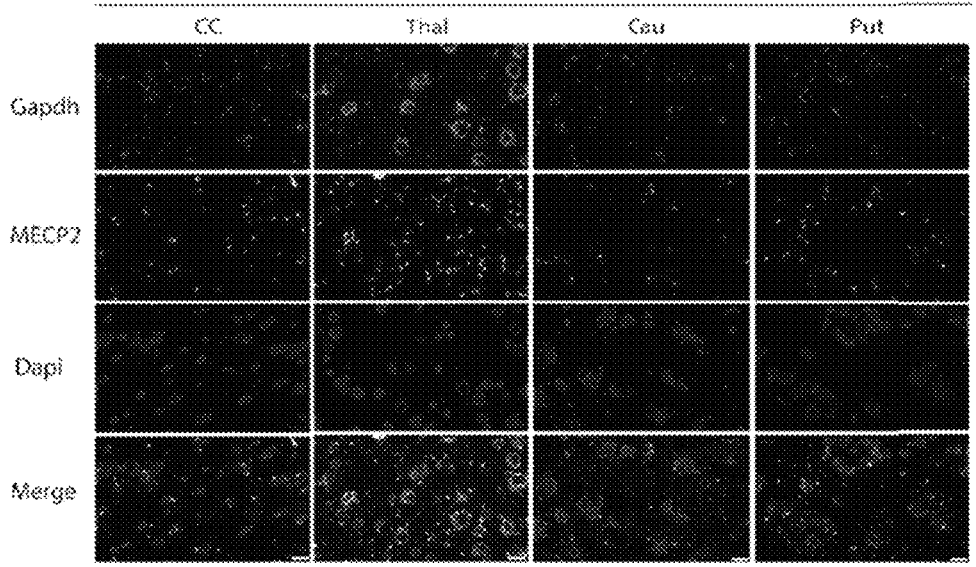
Figure 21:
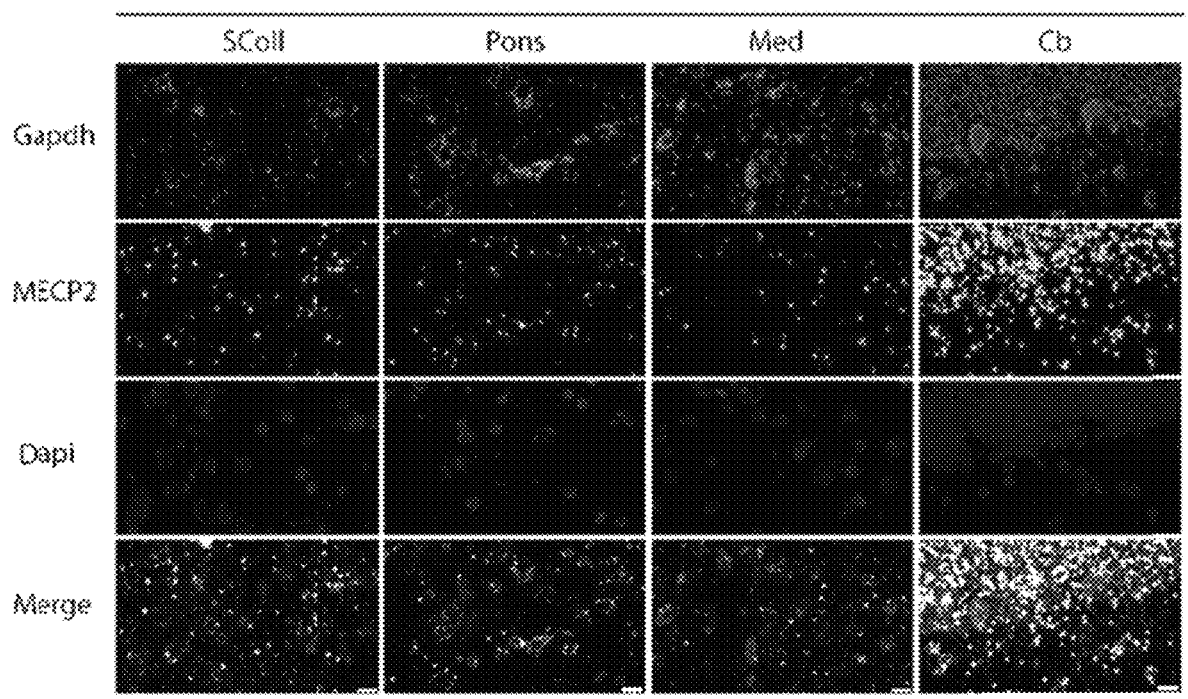
Figure 21:
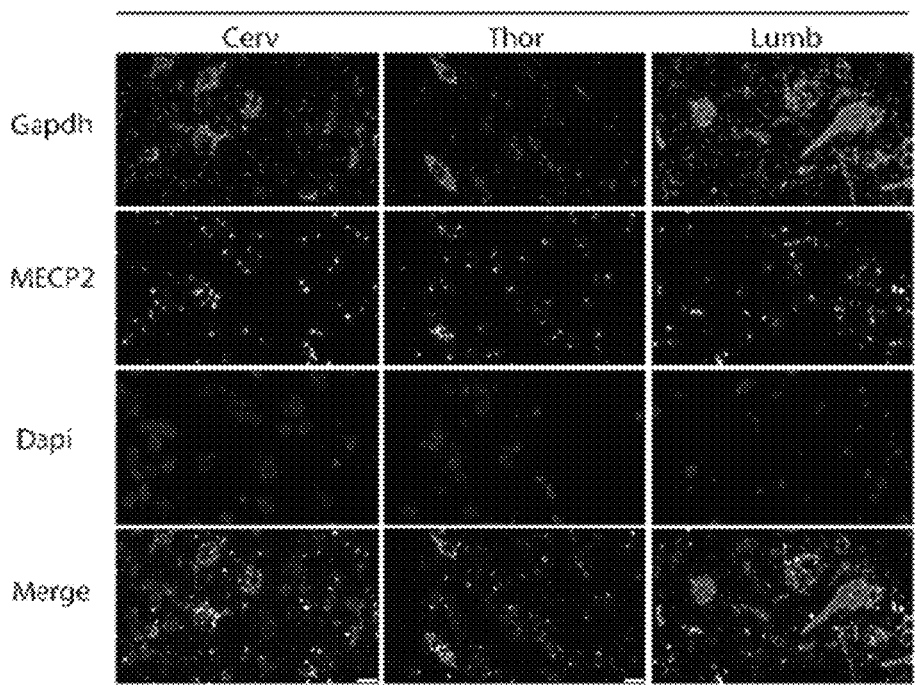

Two 12-month-old, male cynomolgus macaques received intrathecal injections of $7.7 \times 10^{12}$ vg/kg of AVXS-201 as described above. Animals persisted for six weeks post injection and were euthanized for analysis of MeCP2 expression. Selected brain regions were analyzed for total MeCP2 expression by immunohistochemistry (FIG. 18). No obvious elevations of MeCP2 were detected in cortical and subcortical regions nor proximal to the injection site (lumbar spinal cord). Importantly, these data also fail to show any gross abnormalities in tissues from animals that received AVXS-201 injection. To further examine transgene expression, brain regions were homogenized and compared against historical control tissue from animals from the same colony (FIG. 19). Samples of occipital and temporal cortices, hypothalamus, lumbar spinal cord, thalamus, amygdala, hippocampus and cerebellum were analyzed by western blot for total MeCP2 expression. Across all of the regions examined no region showed a >2× level of MeCP2 expression above controls. Elevated MeCP2 was detected in the hypothalamus and amygdala which are regions proximal to 3$^{rd}$ ventrical and lateral ventrical, respectively, but not the cerebellum. Further, the lumbar spinal cord which is proximal to the injection site did not show elevated MeCP2 levels. These data suggest that the combination of viral dose and expression construct are regulating MECP2 expression. Further, in situ hybridization (ISH) was performed to detect vector derived transcript and determine distribution in the brain at 6 weeks and 18 months post injection (FIGS. 20 and 21). All regions examined in the brain and spinal cord (occipital cortex, temporal cortex, hippocampus, corpus callosum, thalamus, caudate, putamen, superior colliculus, pons, medulla, cerebellum, cervical, thoracic and lumbar spinal cord) showed expression of vector derived transcript that was not present in tissues from control treated animals. These data show a specificity of the ISH probe for vector derived MECP2 transcript and show that the AVXS-201 promoter construct is functional in NHP nervous system tissue. These data show that AVXS-201 distributes broadly throughout the CNS when administered via lumbar puncture and expresses at physiological levels.

Disclosure from Provisional Patent Application No. 62/423,618 which is Incorporated by Reference Herein in its Entirety Gene Therapy for Rhett Syndrome Gene therapy to restore the transcription factor MeCP2 appears to be a feasible strategy for treating Rett syndrome, a progressive neurodevelopmental disorder leading to apparent autistic behavior, loss of motor function, and early death. We have developed an adeno-associated virus serotype 9 (AAV9) expressing human MECP2 under the control of a truncated endogenous promoter. The purpose of this work is to assess the efficacy and safety of this vector in mice (MeCP2 null and wild type) and non-human primates. Through continued research, our goal is to bring this treatment from the bench to the bedside.

```
AAV9-P545-MeCP2
Promoter region sequence (mouse MeCP2
promoter fragment; SEQ ID NO: 2)
GTGAACAACGCCAGGCTCCTCAACAGGCAACTTTGCTACTTCTACAGAAA

ATGATAATAAAGAAATGCTGGTGAAGTCAAATGCTTATCACAATGGTGAA

CTACTCAGCAGGGAGGCTCTAATAGGCGCCAAGAGCCTAGACTTCCTTAA

GCGCCAGAGTCCACAAGGGCCCAGTTAATCCTCAACATTCAAATGCTGCC

CACAAAACCAGCCCCTCTGTGCCCTAGCCGCCTCTTTTTTCCAAGTGACA

GTAGAACTCCACCAATCCGCAGCTGAATGGGGTCCGCCTCTTTTCCCTGC

CTAAACAGACAGGAACTCCTGCCAATTGAGGGCGTCACCGCTAAGGCTCC

GCCCCAGCCTGGGCTCCACAACCAATGAAGGGTAATCTCGACAAAGAGCA

AGGGGTGGGGCGCGGGCGCGCAGGTGCAGCAGCACACAGGCTGGTCGGGA

GGGCGGGGCGCGACGTCTGCCGTGCGGGGTCCCGGCATCGGTTGCGCGCG

CGCTCCCTCCTCTCGGAGAGAGGGCTGTGGTAAAACCCGTCCGGAAAAC

Coding region sequence (human MeCP2
cds; SEQ ID NO: 3)
ATGGCCGCCGCCGCCGCCGCCGCGCCGAGCGGAGGAGGAGGAGGAGGCGA

GGAGGAGAGACTGGAAGAAAAGTCAGAAGACCAGGACCTCCAGGGCCTCA

AGGACAAACCCCTCAAGTTTAAAAAGGTGAAGAAAGATAAGAAAGAAGAG

AAAGAGGGCAAGCATGAGCCCGTGCAGCCATCAGCCCACCACTCTGCTGA

GCCCGCAGAGGCAGGCAAAGCAGAGACATCAGAAGGGTCAGGCTCCGCCC

CGGCTGTGCCGGAAGCTTCTGCCTCCCCCAAACAGCGGCGCTCCATCATC

CGTGACCGGGGACCCATGTATGATGACCCCACCCTGCCTGAAGGCTGGAC

ACGGAAGCTTAAGCAAAGGAAATCTGGCCGCTCTGCTGGGAAGTATGATG

TGTATTTGATCAATCCCCAGGGAAAAGCCTTTCGCTCTAAAGTGGAGTTG

ATTGCGTACTTCGAAAAGGTAGGCGACACATCCCTGGACCCTAATGATTT

TGACTTCACGGTAACTGGGAGAGGGAGCCCCTCCCGGCGAGAGCAGAAAC

CACCTAAGAAGCCCAAATCTCCCAAAGCTCCAGGAACTGGCAGAGGCCGG

GGACGCCCCAAAGGGAGCGGCACCACGAGACCCAAGGCGGCCACGTCAGA

GGGTGTGCAGGTGAAAAGGGTCCTGGAGAAAAGTCCTGGGAAGCTCCTTG

TCAAGATGCCTTTTCAAACTTCGCCAGGGGGCAAGGCTGAGGGGGTGGG

GCCACCACATCCACCCAGGTCATGGTGATCAAACGCCCCGGCAGGAAGCG

AAAAGCTGAGGCCGACCCTCAGGCCATTCCCAAGAAACGGGGCCGAAAGC

CGGGGAGTGTGGTGGCAGCCGCTGCCGCCGAGGCCAAAAAGAAAGCCGTG

AAGGAGTCTTCTATCCGATCTGTGCAGGAGACCGTACTCCCCATCAAGAA

GCGCAAGACCCGGGAGACGGTCAGCATCGAGGTCAAGGAAGTGGTGAAGC

CCCTGCTGGTGTCCACCCTCGGTGAGAAGAGCGGGAAAGGACTGAAGACC

TGTAAGAGCCCTGGGCGGAAAAGCAAGGAGAGCAGCCCCAAGGGGCGCAG

CAGCAGCGCCTCCTCACCCCCCAAGAAGGAGCACCACCACCATCACCACC

ACTCAGAGTCCCCAAAGGCCCCGTGCCACTGCTCCCACCCCTGCCCCCA

CCTCCACCTGAGCCCGAGAGCTCCGAGGACCCCACCAGCCCCCCTGAGCC

CCAGGACTTGAGCAGCAGCGTCTGCAAAGAGGAGAAGATGCCCAGAGGAG

GCTCACTGGAGAGCGACGGCTGCCCCAAGGAGCCAGCTAAGACTCAGCCC

GCGGTTGCCACCGCCGCCACGGCCGCAGAAAAGTACAAACACCGAGGGGA

GGGAGAGCGCAAAGACATTGTTTCATCCTCCATGCCAAGGCCAAACAGAG

AGGAGCCTGTGGACAGCCGGACGCCCGTGACCGAGAGAGTTAGCTGA

PolyA sequence (synthetic; SEQ ID NO: 4)
AATAAAAGATCTTTATTTTCATTAGATCTGTGTGTTGGTTTTTGTGTG
```

While the present invention has been described in terms of various embodiments and examples, it is understood that variations and improvements will occur to those skilled in the art. Therefore, only such limitations as appear in the claims should be placed on the invention.

All documents referred to herein are incorporated by reference in their entirety.

The invention claimed is:

1. A recombinant adeno-associated virus (rAAV) vector comprising a gene cassette comprising a promoter consisting of the nucleotide sequence of SEQ ID NO: 2, an SV40 intron, a polynucleotide sequence encoding a methyl-CpG-binding protein 2 (MECP2) and a synthetic polyadenylation signal, wherein the gene cassette is flanked by a mutant AAV2 inverted terminal repeat and a wild type inverted terminal repeat.

2. The rAAV vector of claim 1, wherein the viral vector is self-complementary (scAAV).

3. The rAAV vector of claim 1, wherein the rAAV is rAAV9.

4. The rAAV vector of claim 1, wherein the polynucleotide sequence encoding the MECP2 comprises SEQ ID NO: 3.

5. A recombinant adeno-associated virus (rAAV) vector comprising a gene cassette comprising nucleotides 151-2558 of SEQ ID NO: 1.

6. A virus comprising the rAAV9 vector of claim 3.

7. The virus of claim 6, further comprising one or more capsid proteins.

8. A pharmaceutical composition comprising the rAAV vector of claim 1.

9. A method of treating Rett syndrome in a patient comprising intrathecally administering the rAAV vector of claim 1 to a patient in need thereof.

10. The method of claim 9 further comprising intrathecally administering iohexol, iobitridol, iomeprol, iopamidol, iopentol, iopromide, ioversol or ioxilan, or mixtures of two or more thereof.

11. A virus comprising the rAAV vector of claim 4.

12. The virus of claim 11, further comprising one or more capsid proteins.

13. A pharmaceutical composition comprising the rAAV vector of claim 4.

14. A method of treating Rett syndrome in a patient comprising intrathecally administering the rAAV vector of claim 4 to a patient in need thereof.

15. The method of claim 14 further comprising intrathecally administering iohexol, iobitridol, iomeprol, iopamidol, iopentol, iopromide, ioversol or ioxilan, or mixtures of two or more thereof.

16. A virus comprising the rAAV vector of claim 5.

17. The virus of claim 16, further comprising one or more capsid proteins.

18. A pharmaceutical composition comprising the rAAV vector of claim 5.

19. A method of treating Rett syndrome in a patient comprising intrathecally administering the rAAV vector of claim 5 to a patient in need thereof.

20. The method of claim 19 further comprising intrathecally administering iohexol, iobitridol, iomeprol, iopamidol, iopentol, iopromide, ioversol or ioxilan, or mixtures of two or more thereof.

21. The rAAV vector of claim 5, wherein the viral vector is self-complementary (scAAV).

22. The rAAV vector of claim 5, wherein the rAAV is rAAV9.

23. A virus comprising the rAAV9 vector of claim 22.

24. The virus of claim 23, further comprising one or more capsid proteins.

* * * * *

SEQUENCE LISTING

```
Sequence total quantity: 8
SEQ ID NO: 1            moltype = DNA   length = 2558
FEATURE                 Location/Qualifiers
misc_feature            1..2558
                        note = AVXS-201 genome
misc_feature            1..106
                        note = mutated ITR
misc_feature            151..699
                        note = 546 promoter fragment
misc_feature            729..827
                        note = SV40 intron
misc_feature            848..2344
                        note = hMECP2B cds
misc_feature            2345..2393
                        note = synthetic pA
misc_feature            2418..2558
                        note = ITR
source                  1..2558
                        mol_type = other DNA
                        organism = synthetic construct
SEQUENCE: 1
ctgcgcgctc gctcgctcac tgaggccgcc cgggcaaagc ccgggcgtcg ggcgaccttt 60
ggtcgcccgg cctcagtgag cgagcgagcg cgcagagagg gagtggaatt cacgcgtgga 120
tctgaattca attcacgcgt ggtaccacgc gtgaacaacg ccaggctcct caacaggcaa 180
ctttgctact tctacagaaa atgataataa agaaatgctg gtgaagtcaa atgcttatca 240
caatggtgaa ctactcagca gggaggctct aataggcgcc aagagcctag acttccttaa 300
gcgccagagt ccacaagggc ccagttaatc ctcaacattc aaatgctgcc cacaaaacca 360
gcccctctgt gccctagccg cctcttttt ccaagtgaca gtagaactcc accaatccgc 420
agctgaatgg ggtccgcctc ttttccctgc ctaaacagac aggaactcct gccaattgag 480
ggcgtcaccg ctaaggctcc gccccagcct gggctccaca accaatgaag ggtaatctcg 540
acaaagagca aggggtgggg cgcgggcgcg caggtgcagc agcacacagg ctggtcggga 600
gggcgggcg cgacgtctgc cgtcggggt cccggccatcg gttgcgcgcg cgctccctcc 660
tctcggagag agggctgtgg taaaacccgt ccggaaaacg cgtcgaaggg cgaattctgc 720
agataactgg taagtttagt ctttttttgtc ttttatttca ggtcccggat ccggtggtgg 780
tgcaaatcaa agaactgctc ctcagtcgat gttgccttta cttctaggcc tgtacggaag 840
tgttactatg gccgccgccg ccgccgccgc gccgagcgga ggaggaggag gaggcgagga 900
ggagagactg gaagaaaagt cagaagacca ggacctccag ggcctcaagg acaaacccct 960
caagtttaaa aaggtgaaga agataagaa agaagagaaa gagggcaagc atgagcccgt 1020
gcagccatca gcccaccact ctgctgagcc cgcagaggca ggcaaagcag agacatcaga 1080
agggtcaggc tccgcccccgg ctgtgccgga agcttctgcc tcccccaaac agccgcgctc 1140
catcatccgt gaccggggac ccatgtgatga tgacccacc ctgcctgaag ctgacacg 1200
gaagcttaag caaaggaaat ctggccgctc tgctgggaag tatgatgtgt atttgatcaa 1260
tcccagggga aaagcctttc gctctaaagt ggagttgatt gcgtacttcg aaaaggtagg 1320
cgacacatcc ctgacccta atgatttga cttcacggta actgggagag ggagcccctc 1380
ccggcgagag cagaaaccac ctaagaagcc caaatctccc aaagctccag gaactcccag 1440
aggccgggga cgcccaaag ggagcggcac cacgagaccc aaggcggcca cgtcagaggg 1500
tgtgcaggtg aaaagggtcc tggagaaaag tcctgggaag ctccttgtca agtgcccttt 1560
tcaaacttcg ccagggggca aggctgaggg gggtgggggc accacatcca cccaggtcat 1620
ggtgatcaaa cgccccggca ggaagcgaaa agctgaggcc gaccctcagg ccattcccaa 1680
gaaacgggc cgaaagccgg ggagtgtggt ggcagccgct gccgccgagg ccaaaaagaa 1740
agccgtgaag gagtcttcta tccgatctgt gcaggagacc gtactcccca tcaagaagcg 1800
caagacccgg gagacggtca gcatcgaggt caaggaagtg gtgaagcccc tgctggtgtc 1860
caccctcggt gagaagagcg ggaaaggact gaagaccctg aagagccctg gcggaaaag 1920
caaggagagc agcccaagg ggcgcagcag cagcgcctcc tcaccccca gaaggagca 1980
ccaccaccat caccaccact cagagtcccc aaaggccccc gtgccactgc tcccacccct 2040
gcccccacct ccacctgagc ccgagagctc cgaggacccc accagccccc ctgagcccca 2100
ggacttgagc agcagcgtct gcaaagagga gaatgacccc agggaggct cactggagag 2160
cgacggctgc cccaaggagc cagctaagac tcagcccgcg gttgccaccg ccgccacggc 2220
cgcagaaaag tacaaacacc gagggaggg agagcgcaaa gacattgttt catcctccat 2280
gccaaggcca aacagagag agcctgtgga cagccggacg cccgtgaccg agagagttag 2340
ctgaaataaa agatctttat tttcattaga tctgtgatgt ggttttttgt gtggcatgct 2400
ggggagagat cgatctgagg aaccctagt gatggagttg ccactccct ctctgcgcgc 2460
tcgctcgctc actgaggccg ggcgaccaaa ggtcgcccga cgcccgggct ttgcccgggc 2520
ggcctcagtg agcgagcgag cgcgcagaga gggagtgg                       2558

SEQ ID NO: 2            moltype = DNA   length = 549
FEATURE                 Location/Qualifiers
source                  1..549
                        mol_type = other DNA
                        organism = Mus musculus
SEQUENCE: 2
gtgaacaacg ccaggctcct caacaggcaa ctttgctact tctacagaaa atgataataa 60
agaaatgctg gtgaagtcaa atgcttatca caatggtgaa ctactcagca gggaggctct 120
aataggcgcc aagagcctag acttccttaa gcgccagagt ccacaagggc ccagttaatc 180
ctcaacattc aaatgctgcc cacaaaacca gcccctctgt gccctagccg cctcttttt 240
ccaagtgaca gtagaactcc accaatccgc agctgaatgg ggtccgcctc ttttccctgc 300
ctaaacagac aggaactcct gccaattgag ggcgtcaccg ctaaggctcc gccccagcct 360
gggctccaca accaatgaag ggtaatctcg acaaagagca aggggtgggg cgcgggcgcg 420
```

```
caggtgcagc agcacacagg ctggtcggga gggcggggcg cgacgtctgc cgtgcggggt    480
cccggcatcg gttgcgcgcg cgctccctcc tctcggagag agggctgtgg taaaacccgt    540
ccggaaaac                                                            549
```

| SEQ ID NO: 3 | moltype = DNA  length = 1497 |
|---|---|
| FEATURE | Location/Qualifiers |
| source | 1..1497 |
| | mol_type = other DNA |
| | note = MeCP2B CDS |
| | organism = Homo sapiens |

SEQUENCE: 3
```
atggccgccg ccgccgccgc cgcgccgagc ggaggaggag gaggaggcga ggaggagaga     60
ctggaagaaa agtcagaaga ccaggacctc cagggcctca aggacaaacc cctcaagtct    120
aaaaaggtga agaaagataa gaaagaagag aaagagggca agcatgagcc cgtgcagcca    180
tcagcccacc actctgctga gcccgcagag gcaggcaaag cagagacatc agaagggtca    240
ggctccgccc cggctgtgcc ggaagcttct gcctccccca acagcggcg ctccatcatc     300
cgtgaccggg gacccatgta tgatgacccc accctgcctg aaggctggac acggaagctt    360
aagcaaagga aatctggccg ctctgctggg aagtatgatg tgtatttgat caatcccag    420
ggaaaagcct ttcgctctaa agtggagttg attgcgtact tcgaaaaggt aggcgacaca    480
tccctggacc ctaatgattt tgacttcacg gtaactggga gaggagccc ctcccggcga    540
gagcagaaac cacctaagaa gcccaaatct cccaaagctc caggaactgg cagaggccgg    600
ggacgcccca aagggagcgg caccacgaga cccaaggcgg cacgtcaga gggtgtgcag    660
gtgaaagggg tcctggagaa aagtcctggg aagctccttg tcaagatgcc ttttcaaact    720
tcgccagggg gcaaggctga ggggggtggg gccaccacat ccacccaggt catggtgatc    780
aaacgccccg gcaggaagcg aaaagctgag gccgaccctc aggccattcc caagaaacgg    840
ggccgaaagc cggggagtgt ggtggcagcc gctgccgcg agccaaaaa gaaagccgtg    900
aaggagtctt ctatccgatc tgtgcaggag accgtactcc ccatcaagaa gcgcaagacc    960
cgggagacgg tcagcatcga ggtcaaggaa gtggtaagc ccctgctggt gtccaccctc    1020
ggtgagaaga gcgggaaagg actgaagacc tgtaagagcc ctgggcgaa aagcaaggag    1080
agcagcccca agggcgcag cagcagcgcc tcctcacccc ccaagaagga gcaccaccac    1140
catcaccacc actcagagtc cccaaaggcc cccgtgccac tgctcccacc cctgcccca    1200
cctccacctg agcccgagag ctccgaggac cccaccagcc ccctgagcc caggacttg    1260
agcagcagcc tctgcaaaga ggagaagatg cccagaggag gctcactgga gagcgacggc    1320
tgccccaagg agccagctaa gactcagccc gcggttgcca ccgccgccac ggccgcagaa    1380
aagtacaacc accgaggggga gggagagcgc aaagacattg tttcatcctc catgccaagg    1440
ccaaacagag aggagccctgt ggacagccgg acgcccgtga ccgagagagt tagctga      1497
```

| SEQ ID NO: 4 | moltype = DNA  length = 49 |
|---|---|
| FEATURE | Location/Qualifiers |
| source | 1..49 |
| | mol_type = other DNA |
| | note = Poly A sequence |
| | organism = synthetic construct |

SEQUENCE: 4
```
aataaaagat ctttatttc attagatctg tgtgttggtt ttttgtgtg                49
```

| SEQ ID NO: 5 | moltype = DNA  length = 3093 |
|---|---|
| FEATURE | Location/Qualifiers |
| misc_feature | 1..3093 |
| | note = scAAV9.738.Mecp1 genome |
| misc_feature | 1..106 |
| | note = mutated ITR |
| misc_feature | 198..936 |
| | note = 738 promoter fragment |
| misc_feature | 941..1037 |
| | note = SV40 intron |
| misc_feature | 1138..2643 |
| | note = MeCP2 cds |
| misc_feature | 2709..2890 |
| | note = BGHpA |
| misc_feature | 2953..3093 |
| | note = ITR |
| source | 1..3093 |
| | mol_type = other DNA |
| | organism = synthetic construct |

SEQUENCE: 5
```
ctgcgcgctc gctcgctcac tgaggccgcc cgggcaaagc ccgggcgtcg ggcgaccttt     60
ggtcgcccgg cctcagtgag cgagcgagcg cgcagagagg gagtggaatt cacgcgtgga    120
tctgaattca attcacgcgt ggtaaccgagc tcggatcgac tagtaacgge cgccagtgtg    180
ctggaattcg cccttaatat caaaccatct gattcaacaa tgacagaccg atctcttatg    240
ggcttggcac acaccatctg cccattataa acgtctgcaa agaccaaggt ttgatatgtt    300
gattttactg ttcagcttaa gagtgcgaca tctgctaatt tagtgtaata atacaatcag    360
tagacccttt aaaacaagtc ccttggcttg aacaacgcc aggctcctca acaggcaact    420
ttgctacttc tacagaaaat gataataaag aaatgctttg gaagtcaaat gcttatcca    480
atggtgaact actcagcagg gaggctctaa taggcgccaa gagcctagac ttccttaagc    540
gccagagtcc acaagggccc agttaatcct caacattcaa atgctgccca caaaccagc    600
ccctctgtgc cctagccgcc tctttttcc agtgacagt agaactccac caatccgcag    660
ctgaatgggg tccgcctctt ttcctgcct aaacagacag gaactcctgc caattgaggg    720
cgtcaccgct aaggctccgc cccagcctgg gctccacaac caatgaaggg taatctcgac    780
```

```
aaagagcaag gggtggggcg cgggcgcgca ggtgcagcag cacacaggct ggtcggagg  840
gcggggcgcg acgtctgccg tgcgggtcc  cggcatcggt tgcgcgcgcg ctccctcctc  900
tcggagagag ggctgtggta aacccgtcc  ggaaaactg  gtaagtttag tcttttgtc   960
ttttatttca ggtcccggat ccggtggtgg tgcaaatcaa agaactgctc ctcagtggat 1020
gttgccttta cttctaggcc tgtacggaag tgttacttct gctctaaaag ctgcggaatt 1080
gtacccgcgg ccgatccacc ggttttaagg gccgaggcgg ccagatcttt cgaagatatg 1140
gccgccgctg ccgccaccgc cgccgccgcc gccgcgccga gcggaggagg aggaggaggc 1200
gaggaggaga gactggagga aaagtcagaa gaccaggatc tccagggcct cagagacaag 1260
ccactgaagt ttaagaaggc gaagaaagac aagaaggagg acaaagaagg caagcatgag 1320
ccactacaac cttcagccca ccattctgca gagccagcag aggcaggcaa agcagaaaca 1380
tcagaaagct caggctctgc cccagcagtg ccagaagcct cggcttcccc caaacagcgg 1440
cgctccatta tccgtgaccg gggacctatg tatgatgacc ccaccttgcc tgaaggttgg 1500
acacgaaagc ttaaacaaag gaagtctggc cgatctgctg gaaagtatga tgtatatttg 1560
atcaatcccc agggaaaagc ttttcgctct aaagtagaat tgattgcata ctttgaaaag 1620
gtgggagaca cctccttgga ccctaatgat tttgacttca cggtaactgg gagagggagc 1680
ccctccagga gagagcagaa accacctaag aagcccaaat ctcccaaagc tccaggaact 1740
ggcagggtc  ggggacgccc caagggagc  ggcactggga gaccaaaggc agcagcatca 1800
gaaggtgttc aggtgaaaag ggtcctggag aagagccctg ggaaacttgt tgtcaagatg 1860
cctttccaag catcgcctgg gggtaagggt gagggaggtg gggctaccac atctgcccag 1920
gtcatggtga tcaaacgccc tggcagaaag cgaaaagctg aagctgaccc ccaggccatt 1980
cctaagaaac ggggtagaaa gcctgggagt gtggtggcag ctgctgcagc tgaggccaaa 2040
aagaaagccg tgaaggactg ttccatacgg tctgtgcatg aactgtgct  ccccatcaag 2100
aagcgcaaga cccgggagac ggtcagcatc gaggtcaagg aagtggtgaa gcccctgctg 2160
gtgtccaccc ttggtgagaa aagcgggaag ggactgaaga cctgcaagag ccctgggcgt 2220
aaaagcaagg agagcagccc caaggggcgc agcagcagtg cctcctcccc acctaagaag 2280
gagcaccatc atcaccacca tcactcagag tccacaaagg ccccatgcc  actgctccca 2340
tccccacccc cacctgagcc tgagagctct gaggacccca tcagcccccc tgagcctcag 2400
gacttgagca gcagcatctg caagaagag  aagatgcccc gaggaggctc actgaaaagc 2460
gatggctgcc ccaaggagcc agctaagact cagcctatgg tcgccaccac taccacagtt 2520
gcagaaaagt acaaacaccg aggggaggga gagcgcaagg acattgtttc atcttccatg 2580
ccaaggccaa acagagagga gcctgtggac agccggaccc ccgtgaccga gagagttagc 2640
tgaatcggcg ccgctagcgc ggcgcgtttt aaacccgca  ggtctagaaa gcttatcgat 2700
accgtcgact agagctcgct gatcagcctc gactgtgcct tctagttgcc agccatctgt 2760
tgtttgcccc tcccccgtgc cttccttgac cctggaaggt gccactccca ctgtccttc   2820
ctaataaaat gaggaaattg catcgcattg tctgagtagg tgtcattcta ttctggggg   2880
tggggtgggg caggacagca aggggaagga ttgggaagac aatagcaggc atgctgggga 2940
gagatcgatc tgaggaaccc ctagtgatgg agttggccac tccctctctg cgcgctcgct 3000
cgctcactga ggccgggcga ccaaaggtcg cccgacgccc gggctttgcc cgggcggcct 3060
cagtgagcga gcgagcgcgc agagaggggg tgg                              3093

SEQ ID NO: 6            moltype = DNA  length = 739
FEATURE                 Location/Qualifiers
source                  1..739
                        mol_type = other DNA
                        note = MECP2 promoter
                        organism = Mus musculus
SEQUENCE: 6
tatcaaacca tctgattcaa caatgacaga ccgatctctt atgggcttgg cacacaccat  60
ctgcccatta taaacgtctg caaagaccaa ggtttgatat gttgatttta ctgtcagcct 120
taagagtgcg acatctgcta attagtgta  ataatacaat cagtagaccc tttaaaacaa 180
gtcccttggc ttgaacaac  gccaggctcc tcaacaggca actttgctac ttctacagaa 240
aatgataata aagaaatgct ggtgaagtca aatgctatc  acaatggtga actactcagc 300
agggaggctc taataggcgc caagagccta gacttcctta agcgcagag  tccacaaggg 360
cccagtaat  cctcaacatt caaatgctgc ccacaaaacc agcccctctg tgccctagcc 420
gcctctttt  tccaagtgac agtagaactc caccaatccg tcctgaatg  gggtccgcct 480
cttttcccctg cctaaacaga caggaactcc tgccaattga gggcgtcacc gctaaggctc 540
cgccccagcc tgggctccac aaccaatgaa gggtaatctc gacaaagagc aaggggtggg 600
gcgcgggcgc gcaggtgcag cagcacacag gctggtcggg agggcggggc gcgacgtctg 660
ccgtgcgggg tccggcatc  ggttgcgcgc gcgctccctc ctctcggaga gagggctgtg 720
gtaaaacccg tccggaaaa                                              739

SEQ ID NO: 7            moltype = DNA  length = 1563
FEATURE                 Location/Qualifiers
source                  1..1563
                        mol_type = other DNA
                        note = MECP2alpha
                        organism = Mus musculus
SEQUENCE: 7
gtacccgcgg ccgatccacc ggttttaagg gccgaggcgg ccagatcttt cgaagatatg  60
gccgccgctg ccgccaccgc cgccgccgcc gccgcgccga gcggaggagg aggaggaggc 120
gaggaggaga gactggagga aaagtcagaa gaccaggatc tccagggcct cagagacaag 180
ccactgaagt ttaagaaggc gaagaaagac aagaaggagg acaaagaagg caagcatgag 240
ccactacaac cttcagccca ccattctgca gagccagcag aggcaggcaa agcagaaaca 300
tcagaaagct caggctctgc cccagcagtg ccagaagcct cggcttcccc caaacagcgg 360
cgctccatta tccgtgaccg gggacctatg tatgatgacc ccaccttgcc tgaaggttgg 420
acacgaaagc ttaaacaaag gaagtctggc cgatctgctg gaaagtatga tgtatatttg 480
atcaatcccc agggaaaagc ttttcgctct aaagtagaat tgattgcata ctttgaaaag 540
gtgggagaca cctccttgga ccctaatgat tttgacttca cggtaactgg gagagggagc 600
ccctccagga gagagcagaa accacctaag aagcccaaat ctcccaaagc tccaggaact 660
```

```
ggcaggggtc ggggacgccc caaagggagc ggcactggga gaccaaaggc agcagcatca   720
gaaggtgttc aggtgaaaag ggtcctggag aagagccctg ggaaacttgt tgtcaagatg   780
cctttccaag catcgcctgg gggtaagggt gagggaggtg gggctaccac atctgcccag   840
gtcatggtga tcaaacgccc tggcagaaag cgaaaagctg aagctgaccc ccaggccatt   900
cctaagaaac ggggtagaaa gcctgggagt gtggtggcag ctgctgggac tgaggccaaa   960
aagaaagccg tgaaggagtc ttccatacgg tctgtgcatg agactgtgct ccccatcaag  1020
aagcgcaaga cccgggagac ggtcagcatc gaggtcaagg aagtggtgaa gccccctgctg 1080
gtgtccaccc ttggtgagaa aagcgggaag ggactgaaga cctgcaagag ccctgggcgt  1140
aaaagcaagg agagcagccc caagggggcgc agcacagtg cctcctcccc acctaagaag  1200
gagcaccatc atcaccacca tcactcagag tccacaaagg cccccatgcc actgctccca  1260
tccccacccc cacctgagcc tgagagctct gaggaccccca tcagcccccc tgagcctcag  1320
gacttgagca gcagcatctg caaagaagag aagatgcccc gaggaggctc actggaaagc  1380
gatggctgcc ccaaggagcc agctaagact cagcctatgg tcgccaccac taccacagtt  1440
gcagaaaagt acaaacaccg aggggaggga gagcgcaaaa acattgtttc atcttccatg  1500
ccaaggccaa acagagagga gcctgtggac agccggacgc ccgtgaccga gagagttagc  1560
tga                                                                1563

SEQ ID NO: 8              moltype = DNA   length = 6087
FEATURE                   Location/Qualifiers
misc_feature              1..6087
                          note = Plasmid for AVXS-201 production
misc_feature              1..106
                          note = mutated ITR
misc_feature              151..699
                          note = 546 promotor fragment
misc_feature              729..829
                          note = SV40 intron
misc_feature              848..2344
                          note = hMECP2B
misc_feature              2345..2393
                          note = synthetic pA
misc_feature              2418..2558
                          note = ITR
misc_feature              3309..4259
                          note = kanamycin resistance
misc_feature              4325..4939
                          note = pMB1 ori
source                    1..6087
                          mol_type = other DNA
                          organism = synthetic construct
SEQUENCE: 8
ctgcgcgctc gctcgctcac tgaggccgcc cgggcaaagc ccgggcgtcg ggcgaccttt    60
ggtcgcccgg cctcagtgag cgagcgagcg cgcagagagg gagtgcgaatt cacgcgtgga  120
tctgaattca attcacgcgt ggtaccacgc gtgaacaacg ccaggctcct caacaggcaa   180
ctttgctact tctacagaaa atgataataa agaaatgctg gtgaagtcaa atgcttatca   240
caatggtgaa ctactcagca gggaggctct aataggcgcc aagagcctag acttccttaa   300
gcgccagagt ccacaagggc ccagttaatc ctcaacattc aaatgctgcc cacaaaacca   360
gccccctctgt gccctagccg cctcttttt ccaagtgaca gtagaactcc accaatccgc   420
agctgaatgg ggtccgcctc ttttcctgc ctaaacagac aggaactcct gccaattgag    480
ggcgtcaccc ctaaggctcc gccccagcct gggctccaca accaatgaag ggtaatctcg   540
acaaagagca aggggtgggg cgcgggcgcg caggtgcagg agcacacagg ctggtcggga   600
gggcgggggcg cgacgtctgc cgtgcggggt cccggcatcg gttgcgcgcg cgctccctcc   660
tctcggagag agggctgtgg taaaacccgt ccggaaaacg cgtcgaaggg cgaattctgc   720
agataactga taagtttagt ctttttttgtc ttttatttca ggtcccggat ccggtggtgg   780
tgcaaatcaa agaactgctc ctcagtcgat gttgccttta cttctaggcc tgtacggaag   840
tgttactatg gccgccgccg ccgccgcgc gccgagcgga ggaggaggag gaggcgagga   900
ggagagactg gaagaaaagt cagaagacca ggacctccag ggcctcaagg acaaacccct   960
caagtttaaa aaggtgaaga agataagaa agaagagaaa gagggcaagc atgagcccgt  1020
gcagccatca gcccaccact ctgctgagcc cgcagaggca ggcaaagcag agacatcaga  1080
agggtcaggc tccgccccgg ctgtgccgga agcttctgcc tccccccaaac agcggcgctc  1140
catcatccgt gaccggggac ccatgtgatga tgacccccacc ctgcctgaag ctgacacg    1200
gaagcttaag caaaggaaat ctggccgctc tgctgggaag tatgatgtgt atttgatcaa  1260
tccccaggga aaagcctttc gctctaaagt ggagttgatt gcgtacttcg aaaaggtagg  1320
cgacacatcc ctgaccctta atgattttga cttcacggta actggagagg ggagcccctc  1380
ccggcgagag cagaaccac ctaagaagcc caaatctccc aaagctccag gaactggcag   1440
aggccgggga cgccccaaag ggagcggcac cacgagaccc aaggcggcca cgtcagaggg  1500
tgtgcaggtg aaaaggggtcc tggagaaaag tcctgggaag ctccttgtca agatgccttt  1560
tcaaacttcg ccaggggggca aggctgaggg gggtggggcc accacatcca cccaggtcat  1620
ggtgatcaaa cgccccggg gaagcgaaaa gctgaggcc gaccctcagg ccattcccaa   1680
gaaacgggc gaaagccgg ggagtgtggt ggcagccgct gccgccgagg ccaaaaagaa    1740
agccgtgaag gagtcttcta tccgatctgt gcaggagacc gtactcccca tcaagaagcg  1800
caagacccgg gagacggtca gcatcgaggt caaggaagtg gtgaagcccc tgctggtgtc  1860
cacctcggt gagaagagcg ggaaggact gaagacctgt aagagccctg gcggaaaag    1920
caaggagagc agccccaagg ggcgcagcag cagcgcctc tcacccccca agaaggacca    1980
ccaccaccat caccaccact cagagtcccc aaaggccccc gtgccactgc tcccacccct  2040
gcccccacct ccacctgagc ccgagagctc cggaccccc accagccccc tgagcccca    2100
ggacttgagc agcagcgtct gcaaagagga gaagatgccc agaggaggct cactggagag  2160
cgacggctgc cccaaggagc cagctaagac tcagcctccgcg gttgccaccg ccgccacggc  2220
cgcagaaaag tacaaacacc gaggggaggg agagcgcaaa gacattgttt catcctccat  2280
```

```
gccaaggcca aacagagagg agcctgtgga cagccggacg cccgtgaccg agagagttag  2340
ctgaaataaa agatctttat tttcattaga tctgtgtgtt ggttttttgt gtggcatgct  2400
ggggagagat cgatctgagg aacccctagt gatggagttg gccactccct ctctgcgcgc  2460
tcgctcgctc actgaggccg ggcgaccaaa ggtcgcccga cgcccgggct ttgcccgggc  2520
ggcctcagtg agcgagcgag cgcgcagaga gggagtggcc cccccccccc cccccccggc  2580
gattctcttg tttgctccag actctcaggc aatgacctga tagcctttgt agagacctct  2640
caaaaatagc taccctctcc ggcatgaatt tatcagctag aacggttgaa tatcatattg  2700
atggtgattt gactgtctcc ggcctttctc acccgtttga atctttacct acacattact  2760
caggcattgc atttaaaata tatgagggtt ctaaaaattt ttatccttgc gttgaaataa  2820
aggcttctcc cgcaaaagta ttacagggtc ataatgtttt tggtacaacc gatttagctt  2880
tatgctctga ggctttattg cttaattttg ctaattcttt gccttgcctg tatgatttat  2940
tggatgttga aatcgcctga tgcggtattt tctccttacg catctgtgcg gtatttcaca  3000
ccgcatatgg tgcactctca gtacaatctg ctctgatgcc gcatagttaa gccagccccg  3060
acacccgcca acactatggt gcactctcag tacaatctgc tctgatgccg catagttaag  3120
ccagccccga cacccgccaa cacccgctga cgcgccctga cgggcttgtc tgctcccggc  3180
atccgcttac agacaagctg tgaccgtctc cgggagctgc atgtgtcaga ggttttcacc  3240
gtcatcaccg aaacgcgcga gacgaaaggg cctcgtgata cgcctatttt tataggttaa  3300
tgtcatgaga ttatcaaaaa ggatcttcac ctagatcctt ttaaattaaa aatgaagttt  3360
taaatcaatc taaagtatat atgagtaaac ttggtctgac agttagaaaa actcatcgag  3420
catcaaatga aactgcaatt tattcatatc aggattatca ataccatatt tttgaaaaag  3480
ccgtttctgt aatgaaggag aaaactcacc gaggcagttc cataggatgg caagatcctg  3540
gtatcggtct gcgattccga ctcgtccaac atcaatacaa cctattaatt tccccctcgtc  3600
aaaaataagg ttatcaagtg agaaatcacc atgagtgacg actgaatccg gtgagaatgc  3660
caaaagttta tgcatttctt tccagacttg ttcaacaggc cagccattac gctcgtcatc  3720
aaaatcactc gcatcaacca aaccgttatt cattcgtgat tgcgcctgag cgaggcgaaa  3780
tacgcgatcg ctgttaaaag gacaattaca aacaggaatc gaatgcaacc ggcgcaggaa  3840
cactgccagc gcatcaacaa tattttcacc tgaatcagga tattcttcta atacctggaa  3900
cgctgttttt ccggggatcg cagtggtgag taaccatgca tcatcaggag tacggataaa  3960
atgcttgatg gtcggaagtg gcataaaattc cgtcagccag tttagtctga ccatctcatc  4020
tgtaacatca ttggcaacgc tacctttgcc atgtttcaga aacaactctg gcgcatcggg  4080
cttcccatac aagcgataga ttgtcgcacc tgattgcccg acattatcgc gagcccattt  4140
atacccatat aaatcagcat ccatgttgga atttaatcgc ggcctcgacg tttcccgttg  4200
aatatgcctc atactcttcc tttttcaata ttattgaagc atttatcagg gttattgtct  4260
catgaccaaa atcccttaac gtgagtttc gttccactga gcgtcagacc cctagaaaa  4320
gatcaaagga tcttcttgag atcctttttt tctgcgcgta atctgctgct tgcaaacaaa  4380
aaaaccaccg ctaccagcgg tggtttgttt gccggatcaa gagctaccaa ctctttttcc  4440
gaaggtaact ggcttcagca gagcgcagat accaaatact gttcttctag tgtagccgta  4500
gttaggccac cacttcaaga actctgtagc accgcctaca tacctcgctc tgctaatcct  4560
gttaccagtg gctgctgcca gtggcgataa gtcgtgtctt accgggttgg actcaagacg  4620
atagttaccg gataaggcgc agcggtcggg ctgaacgggg ggttcgtgca cacagcccag  4680
cttggagcga acgacctaca ccgaactgag atacctacag cgtgagctat gagaaagcgc  4740
cacgcttccc gaagggagaa aggcggacag gtatccggta agcggcaggg tcggaacagg  4800
agagcgcacg agggagcttc cagggggaaa cgcctggtat ctttatagtc ctgtcgggtt  4860
tcgccacctc tgacttgagc gtcgattttt gtgatgctcg tcagggggc ggagcctatg  4920
gaaaaacgcc agcaacgcgg cctttttacg gttcctggcc ttttgctggc cttttgctca  4980
catgttcttt cctgcgttat cccctgattc tgtggataac cgtattaccg cctttgagtg  5040
agctgatacc gctcgccgca gccgaacgac cgagcgcagc gagtcagtga gcgaggaagc  5100
ggaagagcgc ccaatacgca aaccgcctct ccccgcgcgt tggccgattc attaatgcag  5160
ctggcgtaat agcgaagagg cccgcaccga tcgcccttcc caacagttgc gcagcctgaa  5220
tggcgaatgg cgattccgtt gcaatggctg gcggtaatat tgttctggat attaccagca  5280
aggccgatag tttgagttct tctactcagg caagtgatgt tattactaat caaagaagta  5340
ttgcgacaac ggttaatttg cgtgatggac agactctttt actcggtggc ctcactgatt  5400
ataaaaacac ttctcaggat tctggcgtac cgttcctgtc taaatcccct taatcggcc  5460
tcctgtttag ctcccgctct gattctaacg aggaaagcac gttatacgtg ctcgtcaaag  5520
caaccatagt acgcgccctg tagcggcgca ttaagcgcgg cgggtgtggt ggttacgcgc  5580
agcgtgaccg ctacacttgc cagcgcccta gcgcccgctc ctttcgcttt cttcccttcc  5640
tttctcgcca cgttcgccgg ctttccccgt caagctctaa atcgggggct ccctttaggg  5700
ttccgattta gtgctttacg gcacctcgac cccaaaaaac ttgattaggg tgatggttca  5760
cgtagtgggc catcgccctg atagacggtt tttcgccctt tgacgttgga gtccacgttc  5820
tttaatagtg gactcttgtt ccaaactgga acaacactca acctatctc ggtctattct  5880
tttgatttat aagggatttt gccgatttcg gcctattggt taaaaaatga gctgatttaa  5940
caaaaattta acgcgaattt taacaaaata ttaacgctta caatttaaat atttgcttat  6000
acaatcttcc tgttttgggg ctttctga ttatcaaccg gggtacatat gattgacatg  6060
ctagttttac gattaccgtt catcgcc                                     6087
```